(12) United States Patent
Hubel et al.

(10) Patent No.: US 10,314,302 B2
(45) Date of Patent: Jun. 11, 2019

(54) CRYOPRESERVATIVE COMPOSITIONS AND METHODS

(71) Applicant: REGENTS OF THE UNIVERSITY OF MINNESOTA, Minneapolis, MN (US)

(72) Inventors: Allison Hubel, St. Paul, MN (US); Kathryn Lindsay Pollock, Seattle, WA (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/381,530

(22) Filed: Dec. 16, 2016

(65) Prior Publication Data

US 2017/0172138 A1 Jun. 22, 2017

Related U.S. Application Data

(60) Provisional application No. 62/268,155, filed on Dec. 16, 2015.

(51) Int. Cl.
*A01N 1/02* (2006.01)

(52) U.S. Cl.
CPC ......... *A01N 1/0221* (2013.01); *A01N 1/0284* (2013.01)

(58) Field of Classification Search
None
See application file for complete search history.

(56) References Cited

U.S. PATENT DOCUMENTS

| 2012/0128641 A1* | 5/2012 | Austen, Jr. | A01N 1/0221 424/93.7 |
| 2015/0099301 A1* | 4/2015 | Lee | C12N 5/0018 435/408 |

FOREIGN PATENT DOCUMENTS

WO  WO-2007149142 A1 * 12/2007 ............... A01N 1/02

OTHER PUBLICATIONS

Grein, Tanja A; et al; "Alternatives to dimethylsulfoxide for serum-free cryopreservation of human mesenchymal stem cells" International Journal of Artificial Organs, 33, 370-380, 2010 (Year: 2010).*
Wang, Hai-Yan; et al; "Cryopreservation of Umbilical Cord Blood-Derived Mesenchymal Stem Cells Without Dimethyl Sulfoxide" CryoLetters, 32, 81-88, 2011 (Year: 2011).*
Sun, Huan; et al; "Compatible Solutes Improve Cryopreservation of Human Endothelial Cells" CryoLetter, 33, 485-493, 2012 (Year: 2012).*
ATCC TIB-152 Jurkat, Clone E6-1 ATCC® TIB-152™ *Homo sapiens* peripheral. Accessed Jun. 21, 2107, online: https://www. google.com/url?sa=t&rct=j&q=&esrc=s&source=web&cd=2&ved=0ahUKEwio1qfEp8_UAhXH6oMKHcOfBhUQFggvMAE&url=https%3A%2F%2Fwww.atcc.org%2F~%2Fps%2FTIB-152.ashx&usg=AFQjCNEDrZ2-4IkVv-aRTyIiDKB_hZ6vNg&cad=rja.
Abazari, "Engineered Trehalose Permeable to Mammalian Cells" 2015 *PLoS One* 10, e0130323.
Acker, "Measurement of trehalose loading of mammalian cells porated with a metal-actuated switchable pore" Biotechnol. Bioeng. [Internet]. Wiley Subscription Services, Inc., A Wiley Company; 82(5), 525, 2003 [cited Jun. 29, 2016]; Available from: http://doi.wiley.com/10.1002/bit.10599.
Allison, "Hydrogen Bonding between Sugar and Protein Is Responsible for Inhibition of Dehydration-Induced Protein Unfolding" 1999 *Arch. Biochem. Biophys.*, 365(2):289-298.
Arakawa, "The stabilization of proteins by osmolytes" 1985 *Biophys. J.* 47:411-414.
Arakawa, "The basis for toxicity of certain cryoprotectants: A hypothesis" 1990 *Cryobiology*, 27(4):401.
Ayres, "Measuring fiber alignment in electrospun scaffolds: a user's guide to the 2D fast Fourier transform approach" 2008 *J Biomater Sci Polym Ed.*, 19:603-621.
Bahrami, "Theoretical Investigation of Interaction of Sorbitol Molecules with Alcohol Dehydrogenase in Aqueous Solution Using Molecular Dynamics Simulation" 2011 *Cell Biochem. Biophys.*, 59(2):79-88.
Baschenko, "On Raman Spectra of Water, Its Structure and Dependence on Temperature" 2011 *Semicond. Physics, Quantum Electron. Optoelectron.*, 14(1):77-79.
Baust, "Molecular Mechanisms of Cellular Demise Associated with Cryopreservation Failure" 2002 *Cell Preservation Technology* 1:17-31.
Beattie, "Investigation into the Subambient Behavior of Aqueous Mannitol Solutions Using Temperature-Controlled Raman Microscopy" 2007 *Eur. J. Pharm. Biopharm.* 67(2):569-578.
Berendsen, "Gromacs: a message-passing parallel molecular dynamics implementation" 1995 *Comp. Phys. Comm.*, 91:43-56.
Bianco, "Mesenchymal stem cells: revisiting history, concepts, and assays" 2008 *Cell Stem Cell*, 2:313-319.
Bomhoff, "The effects of the flavonoid baicalein and osmolytes on the Mg 2+ accelerated aggregation/fibrillation of carboxymethylated bovine 1SS-alpha-lactalbumin" Sep. 2006 *Arch Biochem Biophys.*, 453(1):75-86.
Branca, "Anomalous Cryoprotective Effectiveness of Trehalose: Raman Scattering Evidences" 1999 *J. Chem. Phys.*, 111(1):281-287.
Brubach, "Signatures of the Hydrogen Bonding in the Infrared Bands of Water" 2005 *J. Chem. Phys.*, 122(18):184509.

(Continued)

*Primary Examiner* — David W Berke-Schlessel
(74) *Attorney, Agent, or Firm* — Mueting, Raasch & Gebhardt, PA

(57) ABSTRACT

This disclosure describes a cryopreservative composition and methods for storing cells. Generally, the cryopreservative composition includes a sugar component and a sugar alcohol component, and is effective for storing and recovering cells without requiring dimethyl sulfoxide (DMSO).

20 Claims, 19 Drawing Sheets
(11 of 19 Drawing Sheet(s) Filed in Color)

(56) References Cited

OTHER PUBLICATIONS

Bruder, "Growth kinetics, self-renewal, and the osteogenic potential of purified human mesenchymal stem cells during extensive subcultivation and following cryopreservation" 1997 *J Cell Biochem.*, 64:278-294.
Bruylants, "Differential Scanning Calorimetry in Life Science: Thermodynamics, Stability, Molecular Recognition and Application in Drug Design" 2011, 2011-2020.
Buchanan, "Preservation of differentiation and clonogenic potential of human hematopoietic stem and progenitor cells during lyophilization and ambient storage" 2010 *PloS one*, 5(9):e12518.
Bunaciu, "Raman Spectroscopy for Protein Analysis" 2014 *Appl. Spectrosc. Rev.*, 4928(Dec).
Candela, "Polygammaglutamate in bacteria" Jun. 2006 *Mol Microbiol.*, 60(5):1091-1098.
Caplan, "The MSC: an injury drugstore" 2011 *Cell Stem Cell*, 9:11-15.
Caplan, "Mesenchymal stem cells as trophic mediators" 2006 *J Cell Biochem* 98:1076-1084.
Carvalho, "Evaluation of bone marrow mesenchymal stem cell standard cryopreservation procedure efficiency" Apr. 2008 *Transplant Proc.*, 40(3):839-841.
Chagastelles, "Biology and applications of mesenchymal stem cells" 2010 *Sci Prog.*, 93:113-127.
Chen, "Enhancement of tolerance of abiotic stress by metabolic engineering of betaines and other compatible solutes" 2002 *Curr Opin Plant Biol.*, 5(3):250-257.
Chinnadurai, "Cryopreserved Mesenchymal Stromal Cells Are Susceptible to T-Cell Mediated Apoptosis Which Is Partly Rescued by IFNgamma Licensing" 2016 *Stem cells*, 34:2429-2442.
Chinnadurai, "IDO-independent suppression of T cell effector function by IFN-gamma-licensed human mesenchymal stromal cells" 2014 *J Immunol.*, 192:1491-1501.
Chinnadurai, "Actin Cytoskeletal Disruption following Cryopreservation Alters the Biodistribution of Human Mesenchymal Stromal Cells in Vivo" 2014 *Stem Cell Reports* 3(1):60.
Cicerone, "Fast dynamics and stabilization of proteins: Binary glasses of trehalose and glycerol" 2004 *Biophys J.*, 86(6):3836-3845.
Cocks, "Phase Diagram Relationships in Cryobiology" 1974 *Cryobiology*, 11(4):340-358.
Conde, "Membrane transport, sensing and signaling in plant adaptation to environmental stress" 2011 *Plant and Cell Physiology.*, 52(9):1583-1602.
Conrad, "Stabilization and Preservation of *Lactobacillus acidophilus* in Saccharide Matrices" 2000 *Cryobiology*, 41:17.
Cross "The Raman Spectrum and Structure of Water" 1937 *J. Am. Chem. Soc.*, 59(6):1134-1147.
Crowe, "Interactions of sugars with membranes" 1988 *Biochim. Biophys. Acta*, 947:367-384.
Crowe, "Infrared Spectroscopic Carbohydrates Studies on Interactions of Water and with a Biological Membrane" 1984 *Arch Biochem Biophys.*, 232(1):400-407.
Da Silva Meirelles, "In search of the in vivo identity of mesenchymal stem cells" Sep. 2008 *Stem cells*, 26:2287-2299.
D'Arrigo, "Raman Scattering and Structure of Normal and Supercooled Water" 1981 *J. Chem. Phys.*, 75(9):4264-4270.
Dariolli, "Porcine adipose tissue-derived mesenchymal stem cells retain their proliferative characteristics, senescence, karyotype and plasticity after long-term cryopreservation" Jul. 2013 *PLoS One*, 8:e67939.
Dashnau, "Hydrogen Bonding and the Cryoprotective Properties of Glycerol/water Mixtures" 2006 *J. Phys. Chem. B*, 110(27):13670-13677.
De Veij "Reference database of Raman spectra of pharmaceutical excipients" 2009 *J. Raman Spectrosc.*, 40(3):297.
Dijkstra-Tiekstra, "Optimization of the freezing process for hematopoietic progenitor cells: effect of precooling, initial dimethyl sulfoxide concentration, freezing program, and storage in vapor-phase or liquid nitrogen on in vitro white blood cell quality" 2014 *Transplantation and Cellular Engineering*, 54:3155.
Dominici, "Minimal criteria for defining multipotent mesenchymal stromal cells" The International Society for Cellular Therapy position statement 2006 *Cytotherapy*, 8(4):315-317.
Dong, "Freezing-Induced Phase Separation and Spatial Microheterogeneity in Protein Solutions" 2009 *J. Phys. Chem. B*, 113(30):10081-10087.
Dong, "Interactions among pre-cooling, cryoprotectants, cooling, and thawing for sperm cryopreservation in rhesus monkeys" 2009 *Cryobiology*, 59(3):268.
Dong, "Spatial distribution of the state of water in frozen mammalian cells" Oct. 2010 *Biophysical Journal*, 99(8):2453-2459.
Dudakovic, "High-resolution molecular validation of self-renewal and spontaneous differentiation in adipose-tissue derived human mesenchymal stem cells cultured in human platelet lysate" Oct. 2014 *J Cell Biochem.*, 115(10):1816-1828.
Dudakovic, "Epigenetic Control of Skeletal Development by the Histone Methyltransferase Ezh2" Sep. 2015 *J Biol Chem.*, 290(46): 27604-27617.
Durickovic, "Water-ice Phase Transition Probed by Raman Spectroscopy" 2011 *J. Raman Spectrosc.*, 42(6): 1408-1412.
Eroglu, "Intracellular trehalose improves the survival of cryopreserved mammalian cells" 2000 *Nat. Biotechnol.* [Internet] 18.
Fahy, "Chapter 2 Principles of Cryopreservation by Vitrification" 2015 *Methods Mol. Biol.*, 1257.
Fahy, "Cryoprotectant toxicity and cryoprotectant toxicity reduction: in search of molecular mechanisms" Jun. 1990 *Cryobiology*, 27:247-268.
Feigenbaum, "Prescription of resistance training for health and disease" Jan. 1999 *Med Sci Sports Exerc.*, 31(1):38-45.
Food and Drug Administration (FDA). "GRAS Substances (SCOGS) Database, Mar. 18, 2015" 2015.Online: http://www.fda.gov/Food/IngredientsPackagingLabeling/GRAS/SCOGS/ucm2006852.htm>.
Food and Drug Administration (FDA). Inactive Ingredient Search for Approved Drug Products. Nov. 25, 2015. Accessed Jun. 20, 2017 online: http://www.accessdata.fda.gov/scripts/cder/iig/index.cfm.
Forte, "Hepatocyte growth factor effects on mesenchymal stem cells: proliferation, migration, and differentiation" 2006 *Stem cells*, 24:23-33.
François, "Cryopreserved mesenchymal stromal cells display impaired immunosuppressive properties as a result of heat-shock response and impaired interferon-γ licensing" 2012 *Cytotherapy*, 14(2):147-152.
Francois, "Human MSC suppression correlates with cytokine induction of indoleamine 2,3-dioxygenase and bystander M2 macrophage differentiation" Jan. 2012 *Mol Ther.*, 20:187-195.
Freimark, "Systematic parameter optimization of a $Me_2SO$- and serum-free cryopreservation protocol for human mesenchymal stem cells" 2011 *Cryobiology*, 63:67.
Galipeau, "International Society for Cellular Therapy perspective on immune functional assays for mesenchymal stromal cells as potency release criterion for advanced phase clinical trials" Feb. 2016 *Cytotherapy*, 18:151-159.
Galipeau, "The mesenchymal stromal cells dilemma—does a negative phase III trial of random donor mesenchymal stromal cells in steroid-resistant graft-versus-host disease represent a death knell or a bump in the road?" Jan. 2013 *Cytotherapy*, 15:2-8.
Gangopadhyay, "Temperature dependent Raman and DFT study of creatine" 2015 *Spectrochim. Acta. A. Mol. Biomol. Spectrosc. Elsevier B.V.*; 150:9.
Golovanov, "A Simple Method for Improving Protein Solubility and Long-Term Stability" 2003 *JACS* 14:8933-8939.
Gomez-Fernandez, "Effect of different monosaccharides and disaccharides on boar sperm quality after cryopreservation" 2012 *Anim. Reprod. Sci.* 133, 109-116.
Goodrich, "Alterations in membrane surfaces induced by attachment of carbohydrates" May 1991 *Biochemistry* 30(21):5313.
Graf, "The Multifunctional Role of Ectoine as a Natural Cell Protectant" Jul.-Aug. 2008 *Clin. Dermatol.*, 26 (4), 326-333.

(56) References Cited

OTHER PUBLICATIONS

Grein, "Alternatives to dimethylsulfoxide for serum-free cryopreservation of human mesenchymal stem cells" 2010 *Int J Artif Organs*, 33(6):370-380.
Gruenloh, "Characterization and in vivo testing of mesenchymal stem cells derived from human embryonic stem cells" Mar. 2011 *Tissue Eng Part A*, 17:1517-1525.
Guo, "Osmolyte-induced perturbations of hydrogen bonding between hydration layer waters: Correlation with protein conformational changes" 2009 *The Journal of Physical Chemistry B.*, 113(52): 16632-16642.
Gurtovenko, "Modulating the structure and properties of cell membranes: The molecular mechanism of action of dimethylsulfoxide" 2007 *The Journal of Physical Chemistry B.*, 111(35):10453-10460.
Gusta, "The Effect of Water, Sugars, and Proteins on the Pattern of Ice Nucleation and Propagation in Acclimated and Nonacclimated Canola Leaves" Jul. 2004 *Plant Physiol.*, 135(July):1642-1653.
Hahn, "Influence of the Compatible Solute Ectoine on the Local Water Structure: Implications for the Binding of the Protein G5P to DNA" 2015 *J. Phys. Chem. B*, 119(49):15212-15220.
Harkness, "Identification of abnormal stem cells using Raman spectroscopy" Aug. 2012 *Stem Cells Dev.*, 21(12), 2152.
Holthauzen, "Mixed osmolytes: the degree to which one osmolyte affects the protein stabilizing ability of another" 2007 *Protein Sci.* 16, 293-298.
Hubel, "Advancing the preservation of cellular therapy products" Nov. 2011 *Transfusion*, 51 Suppl 4:82S-86S.
Iwatani, "Dimethyl sulfoxide has an impact on epigenetic profile in mouse embryoid body" 2006 *Stem Cells*, 24(11):2549.
Izutsu, "Effect of Cryoprotectants on the Eutectic Crystallization of NaCl in Frozen Solutions Studied by Differential Scanning Calorimetry (DSC) and Broad-Line Pulsed NMR" 1995 *Chem.Pharm. Bull.*, 43(10):1804-1806.
Jehlička, "Use of Raman Spectroscopy for Identification of Compatible Solutes in Halophilic Bacteria" 2012 *Extremophiles* 16(3):507-514.
Johnson, "Differential Scanning Calorimetry as a Tool for Protein Folding and Stability" Mar. 2013 *Arch. Biochem. Biophys.*, 531(1-2):100-109.
Johnson, "Effects of co-solvents on peptide hydration water structure and dynamics" 2010 *Physical Chemistry Chemical Physics*, 12(2):393-405.
Katkov, "DMSO-Free Programmed Cryopreservation of Fully Dissociated and Adherent Human Induced Pluripotent Stem Cells" 2011 *Stem Cells International*.
Kearney, "Effects of Cryobiological Variables on the Survival of Skin Using a Defined Murine Model" 1990 *Cryobiology*, 27:164.
Kemeny, "A simplified implementation of edge detection in MATLAB is faster and more sensitive than fast fourier transform for actin fiber alignment quantification" 2011 *Microsc Microanal.*, 17:156-166.
Khomyakova, "A methylaspartate cycle in haloarchaea" 2011 *Science*, 331(6015):334-337.
Kocherbitov, "Hydration of Lysozyme Studied by Raman Spectroscopy" May 2013 *J. Phys. Chem. B*. 117(17):4981-4992.
Lee, "Spectral Graph Analyses of Water Hydrogen-Bonding Network and Osmolyte Aggregate Structures in Osmolyte-Water Solutions" Nov. 2015 *J. Phys. Chem. B*, 119(45):14402-14412.
Leibo, "The role of cooling rates in low-temperature preservation" 1971 Cryobiology 8, 447-452 (1971).
Lovelock, "Prevention of freezing damage to living cells by dimethyl sulphoxide" 1959 Nature, 183:1394-1395.
Luetzkendorf, "Cryopreservation does not alter main characteristics of Good Manufacturing Process-grade human multipotent mesenchymal stromal cells including immunomodulating potential and lack of malignant transformation" 2015 *Cytotherapy*, 17:186-198.
Lusena, "Ice Propagation in Systems of Biological Interest. III. Effect of Solutes on Nucleation and Growth of Ice Crystals" 1955 *Arch. Biochem. Biophys.* 57(2):277-284.
Lynch, "Biopolymer mediated trehalose uptake for enhanced erythrocyte cryosurvival" 2010 *Biomaterials*, 31(23):6096-6103.

Ma, "Immunobiology of mesenchymal stem cells" 2014 *Cell Death Differ.*, 21:216-225.
MacKenzie, "Non-Equilibrium Freezing Behaviour of Aqueous Systems" 1977 *Philos. Trans. R. Soc. London.Series B, Biol. Sci.*, 278(959):167-189.
Mamidi, "Comparative cellular and molecular analyses of pooled bone marrow multipotent mesenchymal stromal cells during continuous passaging and after successive cryopreservation" 2012 *J Cell Biochem.*, 113:3153-3164.
Mason, "Cell therapy industry: billion dollar global business with unlimited potential" 2011 *Regen Med.*, 6(3):265.
Mata, "Effects of cryopreservation on effector cells for antibody dependent cell-mediated cytotoxicity (ADCC) and natural killer (NK) cell activity ain (51)Cr-release and CD107a assays" 2014 Journal of Immunological Methods, 406:1.
Mathlouthi, "Laser-raman spectra of d-glucose and sucrose in aqueous solution" 1980 *Carbohydr. Res.* 81(2), 203.
Matsumura, "Polyampholytes as cryoprotective agents for mammalian cell cryopreservation" 2010 *Cell Transplant.*, 19(6-7):6-7.
Matsumura, "Polyampholytes as low toxic efficient cryoprotective agents with antifreeze protein properties" 2009 *Biomaterials*, 30(27):4842-4849.
Mazur, "Freezing of living cells: mechanisms and implications" 1984 *Am. J. Physiol.*, 247, C125-42.
McGrath, "Low temperature biotechnology: emerging applications and engineering contributions" New York NY (345 E. 47th St. New York 10017): ASME; 1988.
Mendelovici, "Cryogenic Raman spectroscopy of glycerol" 2000 *J. Raman Spectrosc.* [Internet]. John Wiley & Sons, Ltd.; 31(12), 1121.
Meryman, "Freezing injury and its prevention in living cells" 1974 *Annu. Rev. Biophys . Bioeng.*, 3:341-363.
Meyer, "Identification of an animal sucrose transporter" 1984 *J. Cell. Sci.*, 124:1984.
Mohammed, "Amino acids as cryoprotectants for liposomal delivery systems" 2007 *European journal of pharmaceutical sciences* 30(5):406-413.
Moll, "Do cryopreserved mesenchymal stromal cells display impaired immunomodulatory and therapeutic properties?" Sep. 2014 *Stem Cells.* 32(9):2430.
Moon, "Successful vitrification of human amnion-derived mesenchymal stem cells" 2008 *Human Reproduction* 23:1760.
Nauta, "Immunomodulatory properties of mesenchymal stromal cells" Feb. 2007 *Blood* 110:3499-3506.
Notman, "Molecular basis for dimethylsulfoxide (DMSO) action on lipid membranes" 2006 *J. Am Chem Soc.*, 128(43):13982-13983.
Pall, "Tackling exascale software challenges in molecular dynamics simulations with GROMACS" In: *Markidis* (Ed.) Solving software challenges for exascale, vol. 8759. Springer, Switzerland; 2014. pp. 3-27.
Petersen, "Sorbitol Prevents the Self-Aggregation of Unfolded Lysozyme Leading to an up to 13??C Stabilisation of the Folded Form" Nov. 2004 *J. Biotechnol.*, 114(3):269-278.
Petzold, "Ice Morphology: Fundamentals and Technological Applications in Foods" 2009 *Food Biophys.*, 4(4):378-396.
Plank, "Application of membrane-active peptides for drug and gene delivery across cellular membranes" 1998 *Adv Drug Deliv Rev.*, 34(1):21-35.
Pocivavsek, "Glycerol-Induced Membrane Stiffening: The Role of Viscous Fluid Adlayers" Jul. 2011 *Biophys. J.*, 101(1):118-127.
Poddar, "Effect of monomeric and oligomeric sugar osmolytes on DeltaGD, the Gibbs energy of stabilization of the protein at different pH values: is the sum effect of monosaccharide individually additive in a mixture?" 2008 *Biophys. Chem.*, 138, 120-129.
Polge, "Revival of spermatozoa after vitrification and dehydration at low temperatures" 1949 *Nature*, 164:666.
Pollock, "Optimization of cell freezing in the absence of DMSO" Biomechanical Engineering Industry Day, University of Minnesota, Minneapolis, MN, May 7, 2014.
Pollock, "Clinical mesenchymal stem cell products experience functional changes in response to freezing" 2015 *Cytotherapy* 17(1):38-45.

(56) References Cited

OTHER PUBLICATIONS

Pollock, "Improved Post-Thaw Function and Epigenetic Changes in Mesenchymal Stromal Cells Cryopreserved Using Multicomponent Osmolyte Solutions" Dec. 2016 *Stems Cells and Develop.*, 15 pages.
Pollock, "Algorithm-driven optimization of cryopreservation protocols for transfusion model cell types including Jurkat cells and mesenchymal stem cells" May 2016 *J Tissue Eng Regen Med.*, doi: 10.1002/term.2175. [Epub ahead of print].
Pollock, "Combinations of Osmolytes, Including Monosaccharides, Disaccharides, and Sugar Alcohols Act in Concert During Cryopreservation to Improve Mesenchymal Stromal Cell Survival" 2016 *Tissue Eng Part C Methods* 22(11):999-1008.
Prestrelski, "Dehydration-Induced Conformational Transitions in Proteins and Their Inhibition by Stabilizers" Aug. 1993 *Biophys. J.*, 65(2):661-671.
Proft, "Repressors and upstream repressing sequences of the stress-regulated ENA1 gene in *Saccharomyces cerevisiae*: bZIP protein Skolp confers HOG-dependent osmotic regulation" Jan. 1999 *Mol Cell Biol.*, 19:537-546.
Psaltis, "Enrichment for STRO-1 expression enhances the cardiovascular paracrine activity of human bone marrow-derived mesenchymal cell populations" 2010 *J Cell Physiol.*, 223:530-540.
Ragoonanan, "Interplay between the actin cytoskeleton and the cell membrane during freeze/thaw and osmotic de/rehydration" Cryo Sapporo, Japan: Academic Press; 2009. Summary page.
Ragoonanan, "Response of the cell membrane-cytoskeleton complex to osmotic and freeze/thaw stresses" Dec. 2010 *Cryobiology*, 61:335-344.
Remmele, "Raman Spectroscopic Studies of Hen Egg-White Lysozyme at High Temperatures and Pressures" Aug. 1990 *J Protein Chem.*, 9 (4):475-486.
Rienzo, "Different Mechanisms Confer Gradual Control and Memory at Nutrient- and Stress-Regulated Genes in Yeast" Nov. 2015 *Mol Cell Biol.*, 35:3669-3683.
Rippon, 1970 *Raman Spectroscopy*, 960.
Rosgen, "Synergy in Protein—Osmolyte Mixtures" 2015 *J. Phys. Chem. B.* 119:150.
Rudolph, "Membrane stabilization during freezing: The role of two natural cryoprotectants, trehalose and proline" 1985 *Cryobiology*, 22(4):367-377.
Rygula, "Raman Spectroscopy of Proteins: A Review" 2013 *J Raman Spectrosc.*, 44(8): 1061-1076.
Samson, "Establishing criteria for human mesenchymal stem cell potency" Jun. 2015 *Stem cells*, 33:1878-1891.
Santarius, "Cryopreservation of spinach chloroplast membranes by low-molecular-weight carbohydrates" Feb. 1983 *Cryobiology* [Internet]. Academic Press; 20(1):90.
Sasnoor, "Prevention of apoptosis as a possible mechanism behind improved cryoprotection of hematopoietic cells by catalase and trehalose" 2005 *Transplantation*, 80(9):1251-1260.
Savitzky, "Smoothing and Differentiation of Data by Simplified Least Squares Procedures" 1964 *Anal. Chem.*, 36(8):1627-1639.
Sawangwan, "Glucosylglycerol and glucosylglycerate as enzyme stabilizers" 2010 *Biotechnology journal*, 5(2): 187-191.
Schmittgen, "Analyzing real-time PCR data by the comparative CT method" Jun. 2008 *Nature Protocols*, (3):1101-1108.
Sei, "Growth Rate and Morphology of Ice Crystals Growing in a Solution of Trehalose and Water" 2002 *J. Cryst. Growth*, 240(1-2):218-229.
Sharma, "Mesenchymal stem or stromal cells: a review of clinical applications and manufacturing practices" 2014 *Transfusion* [Internet]. 54(5):1418.
Singh, "Protein and DNA destabilization by osmolytes: The other side of the coin" 2011 *Life Sci.*, 88(3):117-125.
Singh, "Effect of Polyols on the Conformational Stability and Biological Activity of a Model Protein Lysozyme" 2003 *AAPS PharmSciTech* 4(3):E42.
Storn, "Differential evolution—a simple and efficient heuristic for global optimization over continuous spaces" 1997 *J Global Optimiz.*, 11(4):341-359.
Strauss, "Stabilization of Lipid Bilayer Vesicles by Sucrose during Freezing" Apr. 1986 *Proc. Natl. Acad. Sci. U. S. A.*, 83:2422-2426.
Sum, "Molecular Simulation Study of Phospholipid Bilayers and Insights of the Interactions with Disaccharides" Nov. 2003 *Biophys. J.* 85(11):2830-2844.
Thaler, "DMSO is a strong inducer of DNA hydroxymethylation in pre-osteoblastic MC3T3-E1 cells" Jun. 2012 *Epigenetics* 7:635-651.
Todorov, "Comparative studies of different cryopreservation methods for mesenchymal stem cells derived from human fetal liver" 2010 *Cell Biology International* 34:455.
Toner, "Thermodynamics and kinetics of intracellular ice formation during freezing of biological cells" 1990 *J. Appl. Phys.* 67(3), 1582.
Trivedi, "Derivation and immunological characterization of mesenchymal stromal cells from human embryonic stem cells" 2008 *Experimental Hematology*, 36:350.
Tsutsui, "An optimized small molecule inhibitor cocktail supports long-term maintenance of human embryonic stem cells" 2011 *Nature communications* 2:167.
Uchida, "Morphological Investigations of Disaccharide Molecules for Growth Inhibition of Ice Crystals" 2007 *J. Cryst. Growth* 299(1):125-135.
Valeri, "An experiment with glycerol-frozen red blood cells stored at -80 degrees C for up to 37 years" 2000 *Vox Sanguinis* 79:168.
Wang, "Clinical applications of mesenchymal stem cells" 2012 *J Hematol Oncol.*, 5:19.
Wen, "Application of Differential Scanning Calorimetry for Thermal Stability Analysis of Proteins: Qualification of DSC" Mar. 2012 *J. Pharm. Sci.*, 101 (3):955-964.
Windrum, "Variation in dimethyl sulfoxide use in stem cell transplantation: a survey of EBMT centres" 2005 *Bone Marrow Transplantation*, 36:601-603.
Wojdyr, "Fityk: A General-Purpose Peak Fitting Program" 2010 *J. Appl. Crystallogr.*, 43 (5 Part 1):1126-1128.
Yancey, "Living with water stress: evolution of osmolyte systems" 1982 *Science*, 217(4566):1214.
Yancey, "Organic osmolytes as compatible, metabolic and counteracting cytoprotectants in high osmolarity and other stresses" Jun. 2005 *J. Exp. Biol.* 208(Pt 15):2819.

\* cited by examiner (A)

(B)

| Solution | Average osmolarity |
|---|---|
| Full solution | 542 |
| Sucrose | 136 |
| EG | 461 |
| Alanine | 136 |
| Taurine | 138 |
| Ectoine | 218 |
| S-max | 588 |
| EG-max | 526 |
| A-max | 514 |
| T-max | 208 |
| E-max | 237 |

(A)

(B)

(A)

(B)

| Solution | Composition | Ice | Osmolytes 780-920cm⁻¹ | CH(cell) | Intracellular ice formation |
|---|---|---|---|---|---|
| SGC-A | 150mM Sucrose 684mM Glycerol 25mM Creatine |  |  |  | 3/10 |
| SGC-B | 300mM Sucrose 684mM Glycerol 12.5mM Creatine |  |  |  | 10/10 |

CRYOPRESERVATIVE COMPOSITIONS AND METHODS

CROSS-REFERENCE TO RELATED APPLICATION

This application claims priority to U.S. Provisional Patent Application No. 62/268,155, filed Dec. 16, 2015, which is incorporated herein by reference.

GOVERNMENT FUNDING

This invention was made with government support under EB016247 and EB023880 awarded by the National Institutes of Health. The government has certain rights in the invention.

SUMMARY

This disclosure describes, in one aspect, a cryopreservative composition for storing cells. Generally, the cryopreservative composition includes a sugar component and a sugar alcohol component, and is effective for storing and recovering cells without requiring dimethyl sulfoxide (DMSO).

In some embodiments, the sugar component can include trehalose, fructose, sucrose, glucose, or a combination of sugars.

In some embodiments, the sugar alcohol component can include sorbitol, ethylene glycol, inositol, xylitol, mannitol, or a combination of sugar alcohols.

In some embodiments, the cryopreservative composition can further include an additive such as, for example, a small molecule or a combination of small molecules. In some of these embodiments, the additive can include an amino acid or a combination of amino acids. In certain embodiments, the amino acid can include proline, valine, alanine, isoleucine, histidine, taurine, ectoine, betaine, dimethylglycine, ethylmethylglycine, or an RGD peptide.

In some embodiments, the cryopreservative composition can further include a cell. In some of these embodiments, the cell may be a cryopreserved cell. In some of these embodiments, the cryopreserved cell can be a viable recovered cryopreserved cell.

In another aspect, this disclosure describes a method of cryopreserving a cell. Generally, the method includes adding a cell to any embodiment of a cryopreservative composition summarized above, freezing the composition, storing the frozen composition at a temperature below 0° C., thawing the composition, removing the cell from the thawed composition, and culturing the cell under conditions effective for the cell to remain viable.

In some embodiments, freezing the composition can include at least one round of cooling, re-warming, and further cooling.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing executed in color. Copies of this patent or patent application publication with color drawings will be provided by the Office upon request and payment of the necessary fee.

DETAILED DESCRIPTION OF ILLUSTRATIVE EMBODIMENTS

Figure 1:
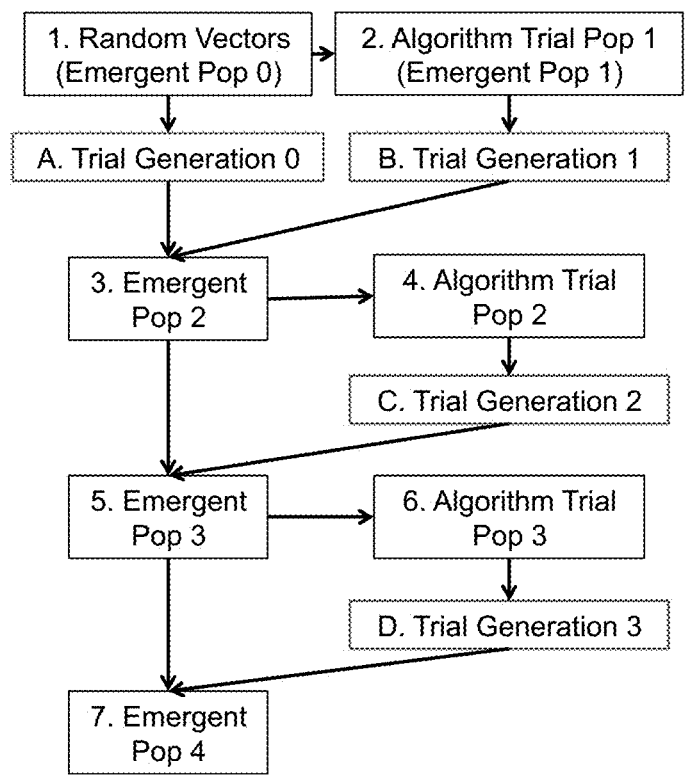
FIG. 1. Differential Evolution (DE) Algorithm flow chart with black boxes representing DE algorithm steps, and red boxes representing experimental steps. The DE algorithm produces a population in gen 0 that randomly spans the parameter space, and a trial population (gen 1) that is based on mutation of gen 0. These are both experimentally tested by the user and the results are input into the DE algorithm, producing an emergent population which is further mutated and iterated in subsequent experiments. As the algorithm converges, an optimum solution can be identified.

Certain medical conditions can be treated using cell therapies. Cells used therapeutically are typically collected in one location, processed in a second location, and administered in a third location. The ability to preserve cells enables coordination between manufacture of the product and patient treatment regimes. Maintaining the biological properties of the cells during transit, processing, and/or storage increases the likelihood that cell therapy employing the cells will be effective.

Conventional methods of cryopreserving cells have involved the use of dimethyl sulfoxide (DMSO). However, DMSO is systemically toxic in humans and can result in side effects ranging from mild (e.g., nausea and vomiting) to severe (e.g., cardiovascular and/or respiratory complications) when transfused in even trace amounts with thawed cells. Also, DMSO increases the mRNA level of the de novo DNA methyltransferase Dnmt3a accompanied by hypermethylation or hypomethylation of many genetic loci. DMSO is thus unsuitable for use with reprogrammed therapeutic cells such as, for example, induced pluripotent stem cells or cells derived from them.

Certain cell types used therapeutically can exhibit altered/diminished in vitro post thaw function. Mesenchymal stem cells can have diminished indoleamine deoxygenase activity and/or altered cytoskeletal function post thaw. Natural killer cells used for immunotherapies also may exhibit diminished post thaw function.

Moreover, survival for many cell types is strongly influenced by cooling rate, with a narrow range of cooling rates over which post thaw survival is optimal. Freezing solution composition also influences cell survival, and changing the composition of the cryopreservation solution may change the cooling rate at which optimum survival is observed. Cryopreservation protocols are often determined empirically by changing composition and cooling rate until the desired outcome is obtained. This process is typically expensive, time consuming, and may not result in an optimized protocol.

A variety of strategies can be used to optimize processes with multiple inputs (e.g., composition of the freezing solution and cooling rate) and outputs (e.g., recovery and viability). This disclosure describes the use of the differential evolution (DE) algorithm (Storn, R. and Price, K., 1997, *J Global Optim* 11(4):341-359) to select composition and cooling rate for cryopreservation solutions. As described in more detail below, DE is applied for the purpose of determining DMSO-free cryopreservation solution formulations for different cell types (e.g., lymphoblasts and mesenchymal stem cells). The methods involved have been adapted to a high-throughput format: small numbers of cells are used and a small number of experiments are required. This type of approach can transform the process of developing freezing protocols by reducing the number of cells and experiments required.

The first phase of this study involved using the DE algorithm to develop a three-component cryopreservation solution used at a single cooling rate (1° C./min). Three components (trehalose, glycerol, and ectoine (TGE)) were selected as components of the exemplary freezing medium used for preservation of Jurkat cells, a hematopoietic model cell type, based on pre-screening of multiple non-DMSO components. For this single cooling rate study, the DE algorithm was programmed to output 18 vector solutions per generation with a weight=0.85 and a crossover=1. Jurkat cells cryopreserved in 10% DMSO at a cooling rate of 1° C./min were used as a control.

Figure 2:
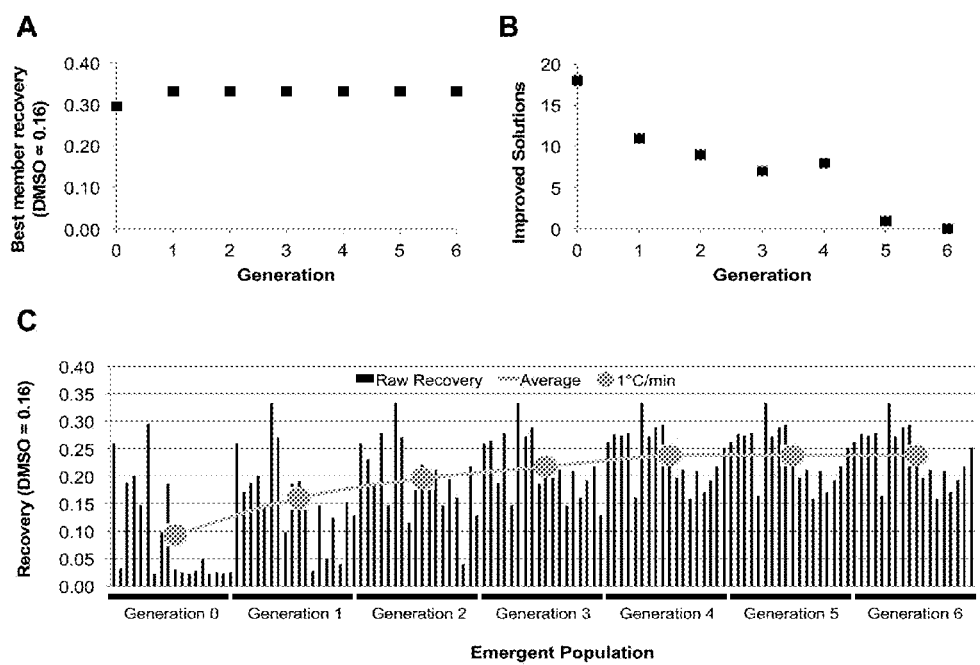
FIG. 2. Trehalose, glycerol, ectoine, 1° C./min DE algorithm results for Jurkat cells. (A) Cumulative best member solution. Recovery associated with the best solution increases and plateaus as the algorithm converges. (B) Number of improved solutions per generation. The number of improved solutions in each generation decreases and reaches zero when the algorithm has converged. (C) Emergent population with the generational average overlaid. The emergent population improves and eventually stops changing as the DE algorithm converges. This is reflected in the generational average, which increases and begins to plateau as the algorithm converges. The optimum composition identified by this run of the algorithm was 150 mM trehalose, 10% glycerol, 0.1% ectoine for Jurkat cells frozen at 1° C./min.

For each generation of solutions tested, the scaled raw recovery of the best solution increased or remained constant (FIG. 2A), while the number of solutions that demonstrated improved recovery tended to decrease for each generation (FIG. 2B). These results together (FIG. 2C) indicate that the DE algorithm converged after six generations (e.g., seven freezing experiments) to an exemplary final solution composition of 150 mM trehalose, 10% glycerol, and 0.1% ectoine (TGE, FIG. 2). The recovery of Jurkat cells frozen in this exemplary TGE solution was 32%, almost twice as high as the recovery of the control (16% recovery in 10% DMSO at 1° C./min).

Cooling rate influences cell survival, and the preferred cooling rate for a given application can depend, at least in part, on the composition of the freezing medium and the cell type being frozen. Therefore, the exemplary TGE solution composition identified for Jurkat cells at a constant cooling rate of 1° C./min may not necessarily be the most effective composition at other cooling rates, and thus may not produce the highest recovery possible. To assess both cooling rate and the composition of the solution, the DE algorithm was programmed to output 27 vector solutions per generation with weight=0.85 and a crossover=1. Solutions were separated into categories based on their DE algorithm defined cooling rate, and were frozen in batches at a cooling rate of 0° C./min, 0.5° C./min, 1° C./min, 3° C./min, 5° C./min, or 10° C./min. Results were normalized and scaled raw recovery is reported, allowing results from all cooling rates and all generations to be compared directly.

As with previous studies, the best member scaled raw recovery increased or remained constant with increasing iterations (FIG. 3A) and the number of improved solutions within each generation tended to decrease (FIG. 3B). The number of solutions frozen at given cooling rates is described by pie charts overlaid at the average recovery of each generation in FIG. 3C. These pie charts show that the DE algorithm quickly identifies poor recovery in solutions frozen at 0° C./min (no freezing, recovery=0) and 0.5° C./min and eliminates these rates after 1-2 generations. In early generations, the majority of solutions with high recovery used cooling rates of 5° C./min and 10° C./min. However, a spike in the number of 1° C./min solutions occurs in Generation 4 after the DE algorithm identifies the same high recovery 1° C./min composition from the constant cooling rate study described in FIG. 2 above. Ultimately at convergence, this DE algorithm run identified a TGE solution containing 300 mM trehalose, 10% glycerol, 0.01% ectoine at a cooling rate of 10° C./min resulted in cell recovery for Jurkat cells of 35% recovery in the TGE solution at 10° C./min (compared to 16% recovery in 10% DMSO at 1° C./min). The DE algorithm converged after seven generations (or eight freezing experiments).

Figure 4:
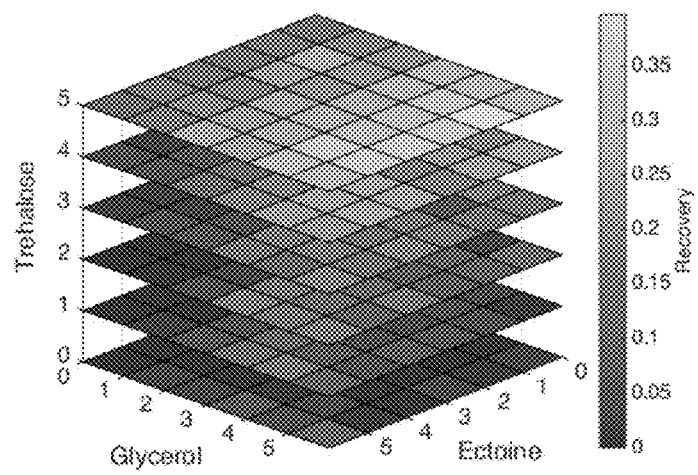
FIG. 4. High throughput concentration study confirmation of Jurkat DE algorithm results. Colors corresponding to recovery values are plotted in squares corresponding to solution compositions within the algorithm parameter space. This concentration study performed at 10° C./min identified the solution composition associated with maximum recovery to be: 300 mM trehalose, 10% glycerol, and 0.01% ectoine (corresponds to the points 5-Trehalose, 5-Glycerol, 1-Ectoine in the heat map above). This composition is the same as the composition identified by the DE algorithm, confirming that it is indeed the optimum within the parameter space at 10° C./min.

High throughput screening of solution compositions was used to confirm that the DE algorithm converged on the true optimum solution composition for a given cooling rate and component concentrations. Samples were frozen and thawed at 10° C./min. Serial dilutions of glycerol, ectoine were combined with dilutions of trehalose and cells suspended in NORMOSOL-R (Hospira, Inc., Lake Forest, Ill.) in 96-well plates. The final concentrations in each well were equal to the full factorial array of concentrations used in the DE algorithm. The results from each well were normalized to a DMSO control included on each plate. This experiment was repeated in triplicate and the recovery results from each individual composition were averaged and are plotted in FIG. 4 (standard deviations were typically below 5%). This study confirmed that a composition of 300 mM trehalose, 10% glycerol, and 0.01% ectoine resulted in the highest recovery for the array tested and confirmed the ability of the DE algorithm to correctly identify an appropriate cell storage solution for cooling at a rate of 10° C./min.

Figure 3:
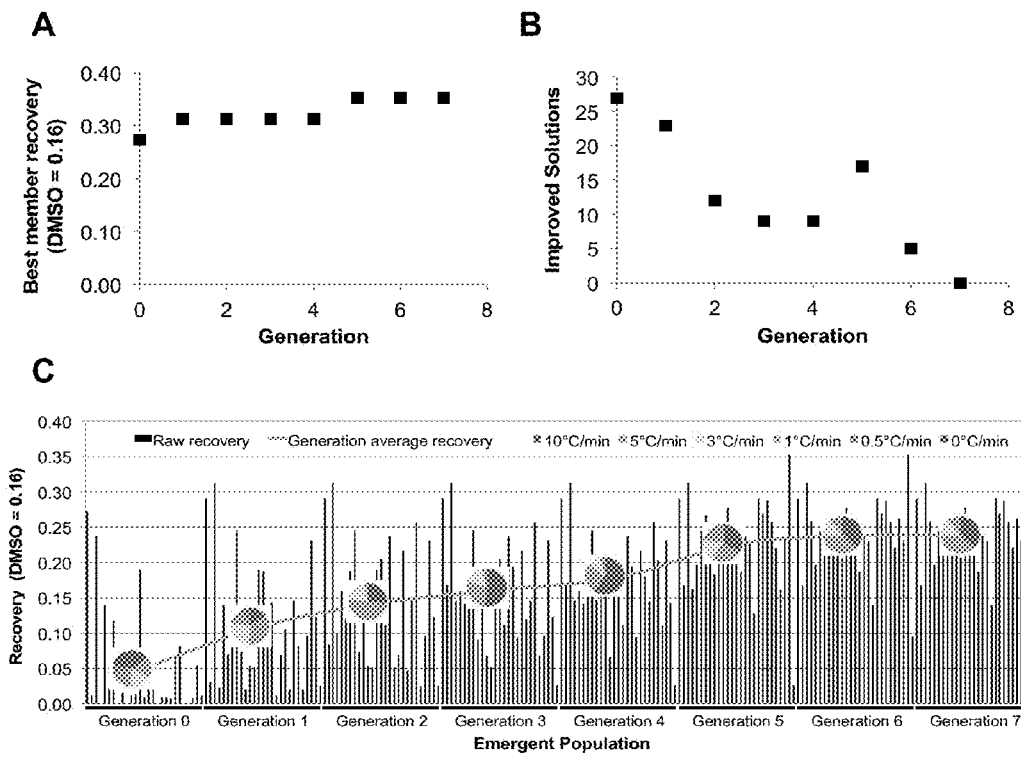
FIG. 3. Trehalose, glycerol, ectoine, cooling-rate DE algorithm results for Jurkat cells. (A) Cumulative best member solution, this increases and plateaus as the DE algorithm converges. (B) Number of improved solutions per generation, this decreases until it reaches zero as the DE algorithm converges. (C) Emergent population with the generational average overlaid. Pie charts at each average show the cooling rate distribution within each generation. The optimum composition identified by this run of the DE algorithm was 300 mM trehalose, 10% glycerol, 0.01% ectoine at 10° C./min cooling.

FIG. 2 and FIG. 3 relate to a three-component TGE solution tested with Jurkat cells. To show that the DE algorithm is capable of converging to freezing solution compositions using different solution components and different cell types, a five-component combination of sucrose, ethylene glycol, alanine, taurine, and ectoine (SEGA) was tested with mesenchymal stem cells at DE algorithm defined concentrations and cooling rates. These components were selected based on pre-screening experiments performed to identify combinations with high potential recovery. The DE algorithm was programmed to output 27 vector solutions per generation with a weight=0.85 and a crossover=1. Experimental testing and result normalization was similar to the methods described above.

Figure 5:
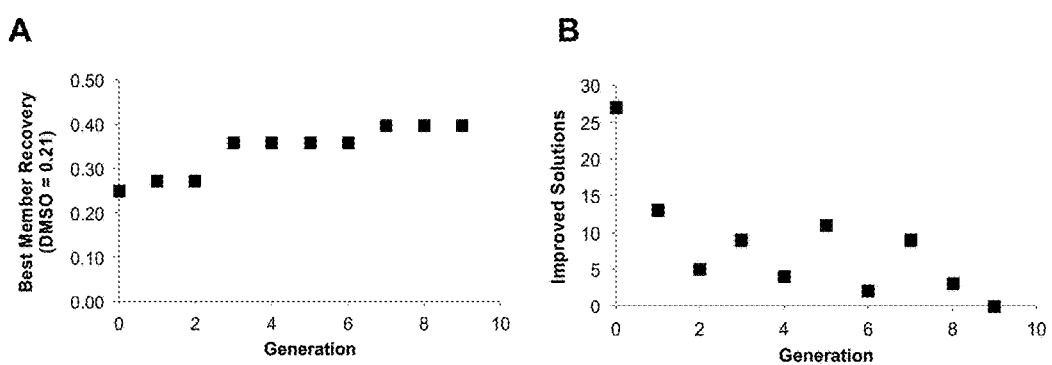
FIG. 5. Sucrose, ethylene glycol, alanine, taurine, ectoine, cooling-rate algorithm results for MSCs. (A) Cumulative best member solution, this increases and plateaus as the DE algorithm converges. (B) Number of improved solutions per generation, this decreases until it reaches zero as the DE algorithm converges. The optimum composition identified by this run of the DE algorithm included: 300 mM ethylene glycol, 1 mM taurine, 1% ectoine with a 1° C./min cooling rate.

As with previous experiments, the cumulative best member composition increased and the number of improved solutions decreased with each generation. At convergence, this run of the DE algorithm identified a SEGA solution of 300 mM ethylene Glycol, 1 mM taurine, and 1% ectoine resulted in recovery for MSCs of 40% at 1° C./min (compared to 21% recovery in 10% DMSO at 1° C./min). Total convergence occurred after nine generations (10 freezing experiments) as evidenced by the increase and plateau of the best member recovery (FIG. 5A) and the decrease in the number of improved solutions per generation (FIG. 5B). Two of the components tested (sucrose and alanine) were not present in the final solution formulation, indicating that the presence of these additives did not improve post thaw survival at this cooling rate.

Freezing experiments were performed in 1 mL vials to determine whether the results with low volumes and small cell numbers in 96-well studies were reproducible when using larger, more clinically relevant volumes. DE algorithm solutions that resulted in maximum recovery were identified for both Jurkats and MSCs at 10° C./min. These solutions are identified as TGE 10° C. (300 mM trehalose, 10% glycerol, and 0.01% ectoine at 10° C./min) and SEGA 10° C. (150 mM sucrose, 300 mM ethylene glycol, 30 mM alanine, 0.5 mM taurine, and 0.02% ectoine at 10° C./min). These solutions were combined with cells, frozen, thawed, and analyzed for viability as described in Example 1. At least nine samples were analyzed for each solution (batches of three or more on at least three different days). These were compared to solutions of cells in 10% DMSO frozen at 1° C./min (the gold standard for both cell types, labeled DMSO 1° C.).

The TGE 10° C. solution resulted in significantly higher viability than SEGA 10° C. and the DMSO 1° C. control (FIG. 6A) for Jurkat cells. Recovery was high across the board (>88%), but not statistically significantly different for any of the solutions tested with Jurkat cells (FIG. 6B). Conversely, MSC viability testing showed no statistically significant differences between solutions (FIG. 6C), while the SEGA 10° C. solution produced significantly higher recovery than either TGE 10° C. or DMSO 1° C. (FIG. 6D). This indicates that results for an individual cell type are unique and can result in significantly higher viability (FIG. 6A) or recovery (FIG. 6D). However, both TGE and SEGA solutions produced acceptable viability and recovery in cell types for which they were not designed, indicating that DE-algorithm-designed solutions may be used to successfully freeze multiple cell types.

Figure 6:
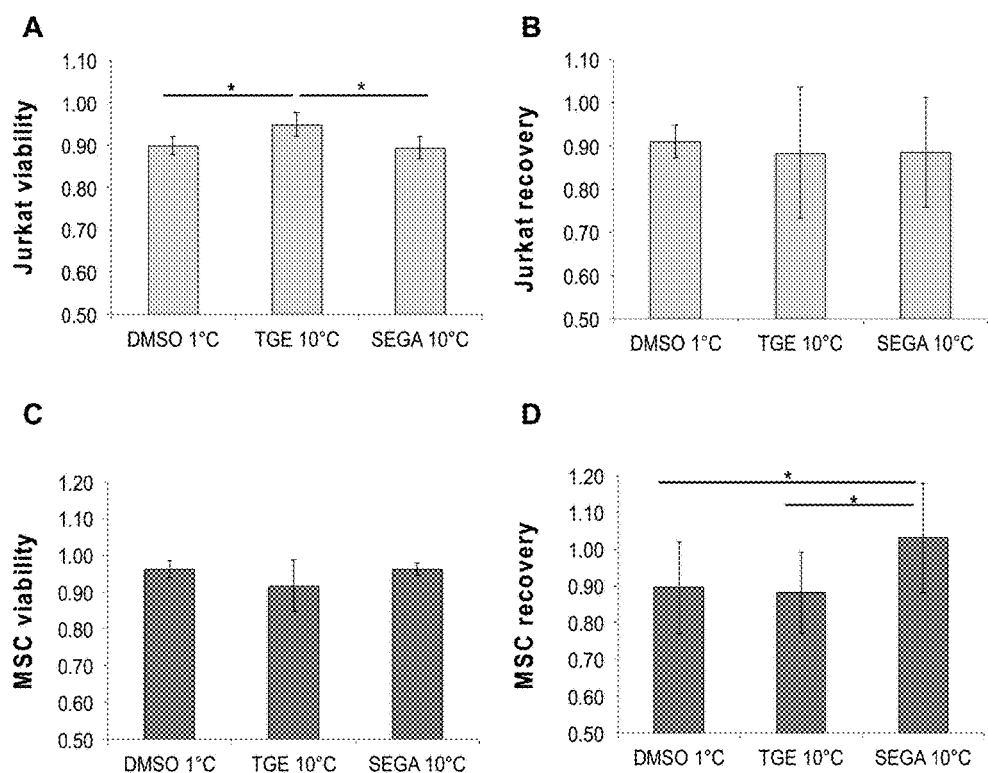
FIG. 6. Scale-up viability and recovery of Jurkat cells (A,B) and mesenchymal stem cells (C,D) frozen in DE algorithm optimized solutions. Each cell type was frozen at 10° C./min in a TGE solution optimized for Jurkats (TGE 10° C.), and a SEGA solution optimized for MSCs (MSC 10° C.). Results were compared to cells frozen in DMSO at 1° C./min (DMSO 1° C.) as it represents the current gold standard for both cell types. Jurkats performed well in both the SEGA 10° C. and TGE 10° C. solutions, and Jurkat viability was significantly higher in TGE 10° C. than both SEGA 10° C. and the DMSO 1° C. control (A). MSCs also performed well in both SEGA 10° C. and TGE 10° C. solutions, and had significantly higher recovery in the SEGA 10° C. solution than both TGE 10° C. and the DMSO 1° C. control (D). Significance markers indicate $p<0.05$.

FIG. 6 also shows that DE algorithm results are scalable. Although the improvement in recovery for optimized solutions in comparison to DMSO is smaller in vial studies than in 96-well studies, this result may be due, at least in part, to the limited difference that is possible when recovery and viability are high. Cumulatively, these results support DE algorithm testing of small volumes of cells and solutions to identify those solutions that produce high viability and recovery at larger volumes.

Current methods of selecting a cryopreservation solution most often use empirical methods—e.g., testing a given composition and cooling rate and measuring post thaw recovery. This disclosure describes using a DE algorithm to evaluate and identify cell storage solutions and/or cooling rates appropriate for a given type of cell. The DE algorithm can be used for different cell types and can concurrently evaluate both solution composition and cooling rate. The DE algorithm as implemented rapidly evaluated both solution composition and cooling rate using less than 200 unique experimental points. Without the aid of the DE algorithm, approximately 7,000 unique experimental data points would have been required to evaluate the compositions tested above. Best member solutions increased and the number of improved solution compositions steadily decreased with each advancing generation, consistent with convergence of the DE algorithm. Convergence was confirmed by high-throughput studies using the same components and the same range of concentrations as the DE algorithm.

The ability to cryopreserve cells in a 96-well format enabled the testing of generations with a large number of solutions (18-27). Freezing cells in 96-well format has been used to improve post thaw recovery of anchorage dependent cells. Cells cryopreserved in a 96-well format are also available commercially and used for drug screening and other applications. For example, conventional preservation of Jurkats cells and MSCs is typically performed using 10% DMSO and a cooling rate of 1° C./min. A limited number of studies have examined vitrification of MSCs and the use of polymers to replace DMSO. This disclosure describes exemplary solutions with multiple components that preserve cell viability without DMSO. This disclosure describes, generally, the combination of two or more cryoprotectants for effective cell cryoprotection. Additionally, these exemplary multi-component compositions result in cell viability and recovery higher than that observed using 10% DMSO, which is an important step forward towards DMSO-free cryopreservation.

Exemplary cryoprotective solutions include those that may be used for storage of lymphocytes. Different combinations of sugars, sugar alcohols, and amino acids were used as cryoprotective agents during freezing of lymphocytes using high throughput screening techniques. Statistical analysis of the data was performed using a Linear Effects Model. The model associated with best fit was determined using Bayesian Information Criteria. A more detailed description of the analysis can be found in Example 2. 128 combinations of sugar, sugar alcohol, and amino acid exhibited the highest predicted recovery rate. The ten best performing combination are given in Table 1.

TABLE 1

Combinations of additives that resulted in the highest post thaw recovery for lymphocytes cryopreserved in these combinations.

| Sugar | Alcohol | Amino acid |
|---|---|---|
| Trehalose | Mannitol | Ectoine |
| Sucrose | Sorbitol | Ectoine |
| Sucrose | Sorbitol | Taurine |
| Sucrose | Sorbitol | Isoleucine |
| Sucrose | Sorbitol | — |
| Trehalose | Mannitol | — |
| Trehalose | Mannitol | Valine |
| Trehalose | Sorbitol | — |
| Trehalose | Xylitol | — |
| Trehalose | Glycerol | — |

The data were further analyzed for highest recovery among the combinations that include sucrose. Sucrose is an additive that is Generally Regarded as Safe (GRAS). Thus, combinations that include sucrose may be of particular interest for regulatory and/or commerciability of storage solutions for cryopreservation of cells for cell therapy applications. Other sugars may be equally suitable, however.

TABLE 2

Combinations with sucrose that result in high recovery.

| Sugar | Alcohol | Amino acid |
|---|---|---|
| Sucrose | Glycerol | Alanine, Creatine, Isoleucine, Taurine, or Valine |
| Sucrose | Arabitol | Creatine, Isoleucine, or Taurine |
| Sucrose | Mannitol | Alanine, Creatine, Isoleucine, Taurine, Proline, or Valine |
| Sucrose | Sorbitol | Alanine, Creatine, Isoleucine, Taurine, Proline, or Valine |
| Sucrose | Xylitol | Creatine, Isoleucine, Taurine, or Valine |
| Sucrose | Glycerol | Alanine, Creatine, Isoleucine, Taurine, or Valine |

Table 2 lists multiple amino acids, each of which can be used in combination with the sugar and sugar alcohol. The listed amino acids may be used alone or in combination with one or more amino acids.

Other exemplary compositions include those that may be used for storage of mesenchymal stem cells. Different combinations of sugars, sugar alcohols, and amino acids were used as cryoprotective agents during freezing of lymphocytes using high throughput screening techniques. Statistical analysis of the data was performed using a Linear Effects Model. The model associated with best fit was determined using Bayesian Information Criteria. A more detailed description of the analysis can be found in Example 2. 76 combinations of sugar, sugar alcohol, and amino acid exhibited the highest predicted recovery rate. The eight best performing combination are given in Table 3.

TABLE 3

Combinations of additives that resulted in the highest post thaw recovery for MSCs cryopreserved in these combinations.

| Sugar | Alcohol | Amino acid |
|---|---|---|
| Sucrose | Glycerol | Isoleucine |
| Sucrose | Glycerol | Ectoine |
| Sucrose | Glycerol | Alanine |
| Sucrose | Mannitol | — |
| Sucrose | Mannitol | Ectoine |

The data were once again further analyzed for highest recovery among the combinations that include sucrose. Sucrose is an additive that is Generally Regarded as Safe (GRAS). Thus, combinations that include sucrose may be of particular interest for regulatory and/or commerciability of storage solutions for cryopreservation of cells for cell therapy applications. Other sugars may be equally suitable, however. All sugar alcohols and additives listed in the combinations in Table 4 below are also GRAS.

TABLE 4

GRAS combinations with sucrose that result in high recovery

| Sucrose | Glycerol | Alanine, Creatine, Isoleucine, Taurine |
| Sucrose | Arabitol | Creatine |
| Sucrose | Mannitol | Creatine, Taurine |
| Sucrose | Sorbitol | Alanine, Creatine, Isoleucine, Taurine, Valine |
| Sucrose | Erythritol | Creatine |
| Sucrose | Inositol | Creatine, Isoleucine |

Table 2 lists multiple amino acids, each of which can be used in combination with the sugar and sugar alcohol. The listed amino acids may be used alone or in combination.

In another evaluation, cells were combined with factorial combinations of the components listed in Table 5, using one component from each category. Plates including cells and solutions were frozen at cooling rates of 1° C./min, 3° C./min, 5° C./min, or 10° C./min.

TABLE 5

Components tested for both Jurkats (lymphocytes) and MSCs

| Sugars (1-300 mM) | Sugar Alcohols (0.1-1.4M) | Additives (1-300 mM) |
|---|---|---|
| Sucrose | Arabitol | Alanine |
| Trehalose | Erythritol | Creatine |
|  | Glycerol | Ectoine |
|  | Inositol | Isoleucine |

TABLE 5-continued

Components tested for both Jurkats (lymphocytes) and MSCs

| Sugars (1-300 mM) | Sugar Alcohols (0.1-1.4M) | Additives (1-300 mM) |
|---|---|---|
| | Mannitol | Proline |
| | Ribitol | Taurine |
| | Sorbitol | Valine |
| | Xylitol | |

Recovery was calculated by dividing the number of live cells post thaw—calculated using a control curve correlating calcein-acetoxymethyl (AM) fluorescence to cell count—by the number of live cells seeded pre-freeze (AO/PI counts taken prior to freezing). Recovery was normalized by dividing by the DMSO recovery on each plate, then multiplying by a standard DMSO recovery for each cooling rate. This normalized recovery was used to compare samples between different plates and different cooling rates.

Statistical analysis of the data was performed using a Linear Effects Model. The model associated with best fit was determined using Bayesian Information Criteria. 128 combinations of sugar, sugar alcohol, and amino acid were found to contain the highest predicted recovery rate for Jurkats, while 76 combinations were found to contain highest predicted recovery rate for MSCs. The ten best combinations for Jurkats are summarized in Table 6 below, while the eight best combinations for MSCs are summarized in Table 7.

TABLE 6

| Sugar | Alcohol | Amino acid |
|---|---|---|
| Trehalose | Mannitol | Ectoine |
| Sucrose | Sorbitol | Ectoine |
| Sucrose | Sorbitol | Taurine |
| Sucrose | Sorbitol | Isoleucine |
| Sucrose | Sorbitol | — |
| Trehalose | Mannitol | — |
| Trehalose | Mannitol | Valine |
| Trehalose | Sorbitol | — |
| Trehalose | Xylitol | — |
| Trehalose | Glycerol | — |

TABLE 7

| Sugar | Alcohol | Amino acid |
|---|---|---|
| Sucrose | Glycerol | Isoleucine |
| Sucrose | Glycerol | Ectoine |
| Sucrose | Glycerol | Alanine |
| Sucrose | — | Ectoine |
| Sucrose | Mannitol | — |
| Sucrose | Mannitol | Ectoine |
| Trehalose | — | Ectoine |

Statistical analysis revealed that the combination of sugar and cooling rate was most influential in predicting recovery. Jurkat cells performed better when frozen with sucrose at 10° C. and 1° C./min, or Trehalose at 5° C./min. MSCs performed better when frozen with sucrose at 3° C. and 5° C./min, or Trehalose at 10° C./min Additionally, statistical analysis revealed positive and negative correlations with recovery for some of the compounds tested. In MSCs, recovery was positively correlated with glycerol and sorbitol. In Jurkat cells, recovery was negatively correlated with erythritol, ribitol, and proline (data not shown). In MSCs, recovery was negatively correlated with proline, valine, erythritol, and ribitol (data not shown).

Figure 7:
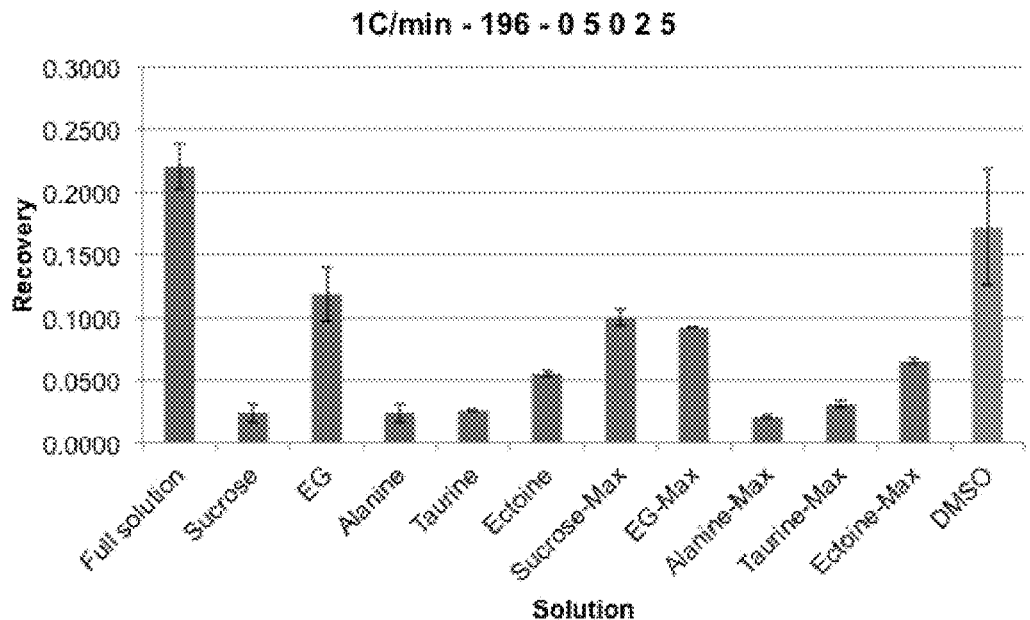
FIG. 7. Osmolarity tests of individual molecules versus solutions designed for storage of MSCs. (A) Mesenchymal stem cells were combined with: a full solution with sucrose, ethylene glycol, alanine, taurine, and ectoine (first column from left); individual components at the same concentration of each component as is present in the full solution (columns 2-6 from the left); individual components at concentrations calculated to produce an osmolarity equal to the full solution osmolarity (columns 7-11 from the left); or a 10% DMSO positive control solution (right column). These results show that the full solution outperformed each individual component both at the concentration that the component is present in the full solution, and full osmolarity concentrations, indicating that the full solution is stabilizing the cells in some way other than by osmolarity alone. (B) Osmolarities (mM) of the solutions tested in (A).

To determine whether results of studies are due to interactions between molecules or just due to the total concentration of cryoprotectants in solution, concentration studies were performed to compare the recovery of cells in a full solution to cells in solutions of each individual cryoprotectant at both their concentration, and a concentration that produced the full solution osmolarity. Results for MSCs are shown in FIG. 7A.

Figure 8:
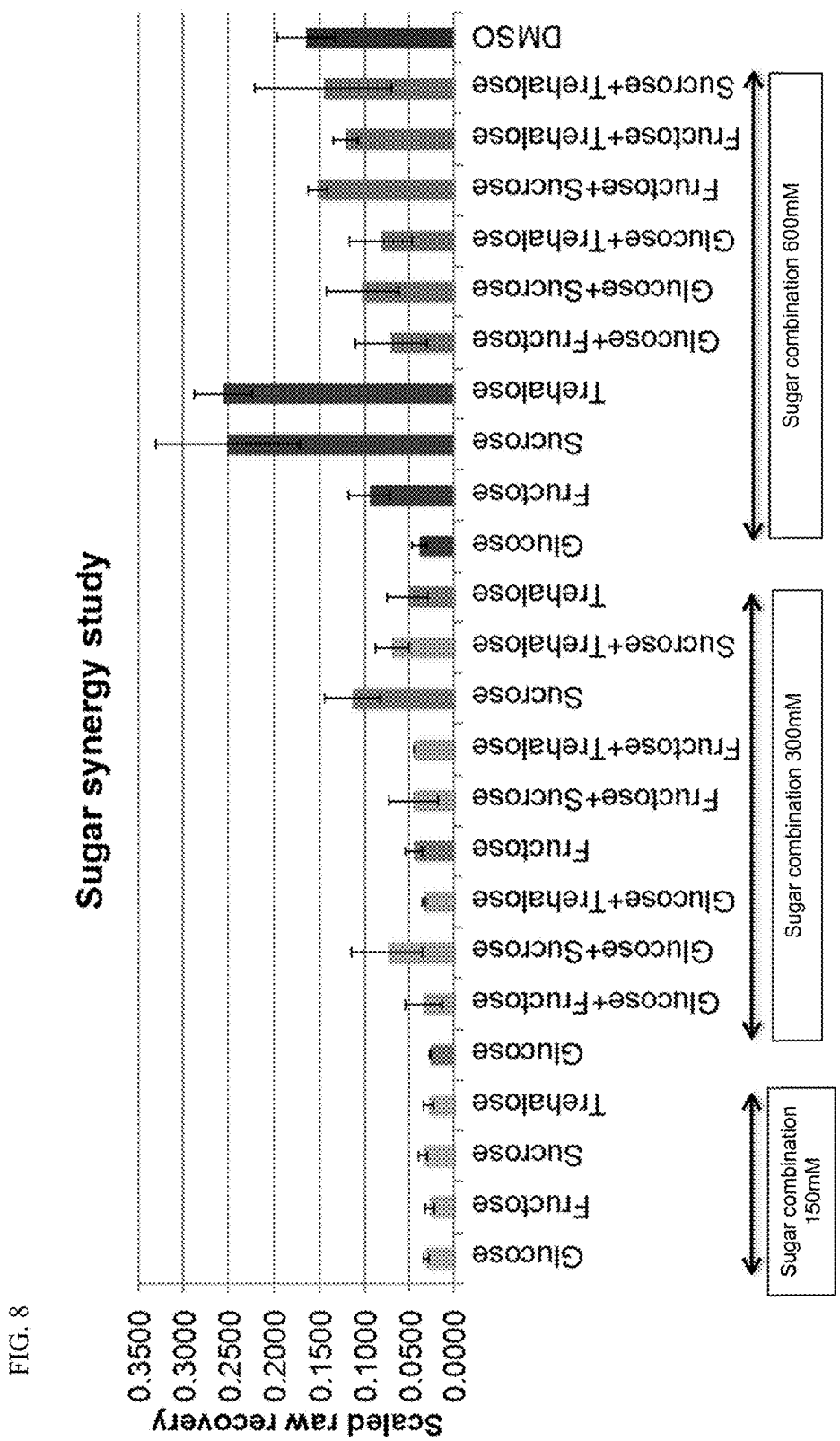
FIG. 8. Sugar synergy study. Jurkat cells were combined with solutions of sugars at the indicated concentrations (150 mM total, 300 mM total, 600 mM total). Solutions were composed of one sugar or equal concentrations of two sugars, totaling the indicated concentration. Increasing the total sugar concentration increased recovery, but multiple sugars at a given total concentration did not produce higher recovery than a single sugar at that concentration. Disaccharides (trehalose, sucrose) outperformed monosaccharides (glucose, fructose).

FIG. 8 shows the results of a study to evaluate whether using multiple components from the same category (e.g., multiple sugars or multiple sugar alcohols) would produce higher recovery. FIG. 8 shows that increasing the total sugar concentration increased recovery of Jurkat cells, but multiple sugars at a given total concentration did not produce higher recovery than a single sugar at that concentration. Although recoveries are high for the 600 mM cases, this is an unrealistic sugar concentration for testing as it approaches the solubility limits for sucrose and trehalose.

Sugar alcohol studies produced similar results, but a few combinations of double sugar alcohols produced recoveries higher than either individual sugar alcohol at the same concentration. Combinations with only GRAS molecules that had favorable expected recovery based on the statistics in ITDD experiments above are indicated in bold face in Table 8.

TABLE 8

| Sugar alcohol #1 | Sugar alcohol #2 |
|---|---|
| Arabitol | Erythritol* |
| | Glycerol |
| | Inositol |
| | Sorbitol |
| Erythritol* | Inositol |
| | Xylitol |
| Glycerol | Inositol |
| Mannitol | Sorbitol |
| | Xylitol |
| Ribitol* | Xylitol |
| Sorbitol | Xylitol |

*sugar alcohols that negatively influenced Jurkat cell recovery

Figure 9:
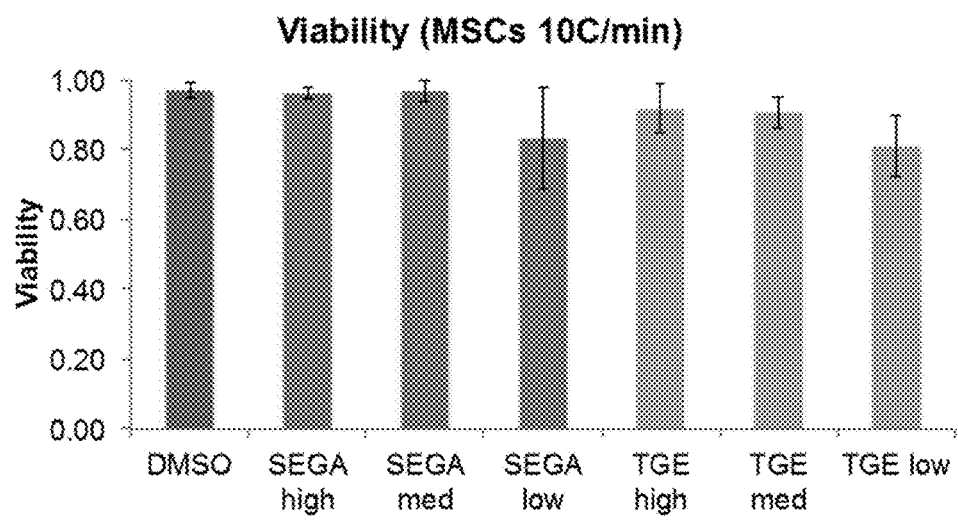
FIG. 9. MSC vial recovery in MSC-designed and non-MSC-designed solutions. MSCs were frozen at a rate of at −10° C./minute in a solution of sucrose, ethylene glycol, alanine, taurine, and ectoine (SEGA) or a solution of trehalose, glycerol, and ectoine (TGE). The SEGA high solution was designed for MSCs while the TGE high solution was designed for Jurkats. The medium solution for each type produced <70% recovery during initial testing; the low solution for each type were produced <40% recovery during initial testing. (A) MSCs had higher viability in SEGA-high and TGE-high than medium and low solutions composed of different concentrations of the same components. (B) MSCs had higher recovery in SEGA-high and TGE-high than medium and low solutions composed of different concentrations of the same components. MSCs frozen with MSC-designed SEGA solutions tended to outperform their TGE counterparts.
Figure 9:
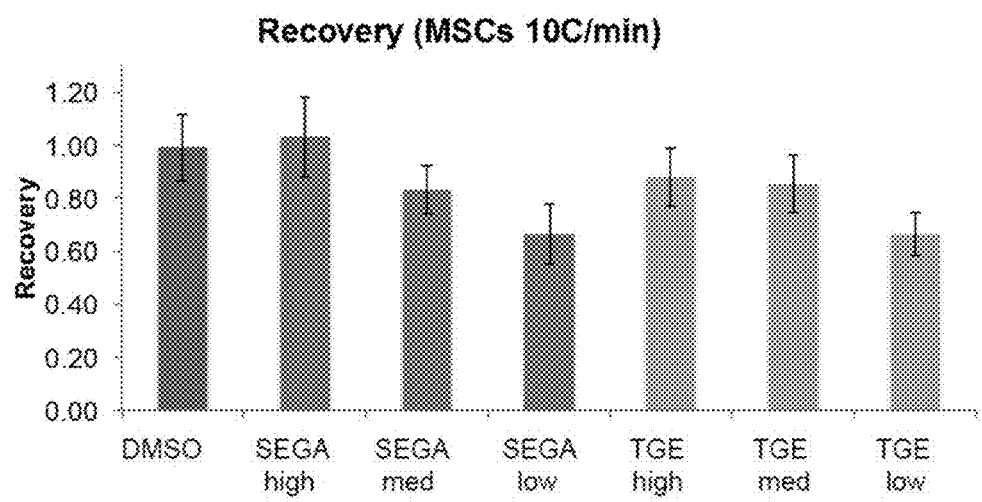

Vial experiments were performed in order to ascertain if the recovery trends observed at the 96-well scale were translatable to larger clinical volumes. Jurkat cells and MSCs were suspended in NORMOSOL-R (Hospira, Inc., Lake Forest, Ill.) and combined stepwise with 2× concentrations of optimized cryopreservation solutions. In addition to running the best cryopreservation solutions, a medium-performing solution and a poor-performing solution containing the same components at different concentrations were also tested. SEGA (sucrose, ethylene glycol, alanine, taurine, ectoine) solutions were tailored for MSCs, while TGE (trehalose, glycerol, ectoine) solutions were tailored for Jurkat cells. MSC experiments were run over at least three different days, with 3-6 vials of each solution in each run. Jurkat cell experiments need higher n; data in FIG. 9 is reflective of a minimum of one run (3 vials) on one day for some of the Jurkat cell samples.

SEGA high recovery was significantly greater than all other experimental solutions, and not significantly different than DMSO for MSCs. Similar experiments were performed with Jurkat cells.

Figure 10:
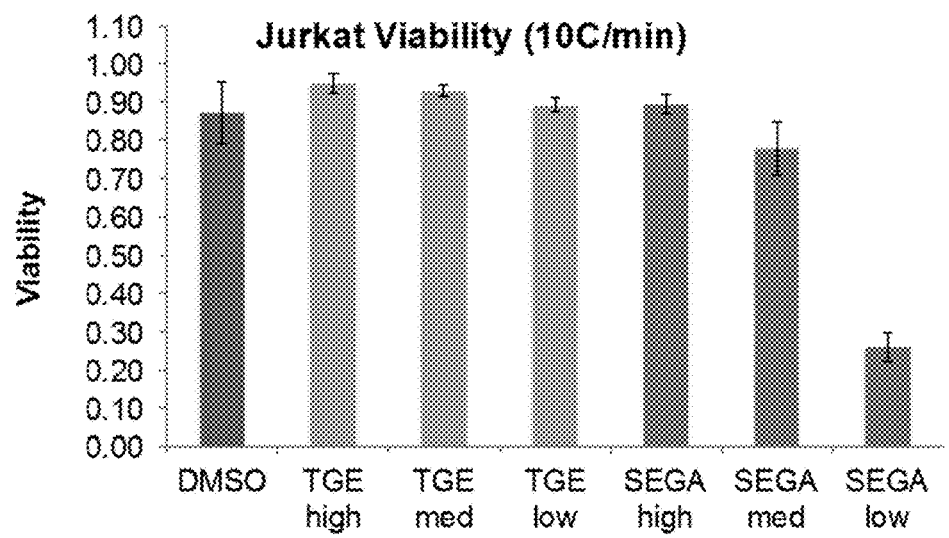
FIG. 10. Jurkat vial recovery in Jurkat-designed and non-Jurkat-designed solutions. Jurkats were frozen at a rate of at −10° C./minute in a solution of trehalose, glycerol, and ectoine (TGE) or in a solution of sucrose, ethylene glycol, alanine, taurine, and ectoine (SEGA). The TGE high solution was designed for Jurkats while the SEGA high solution was designed for MSCs. The medium solution for each type produced <70% recovery during initial testing; the low solution for each type were produced <40% recovery during initial testing. (A) Jurkats had higher viability in TGE-high and SEGA-high than medium and low solutions composed of different concentrations of the same components. (B) Jurkats had higher recovery in TGE-high and SEGA-high than medium and low solutions composed of different concentrations of the same components. Jurkat cells frozen with Jurkat-designed TGE solutions tended to outperform their SEGA counterparts.
Figure 10:
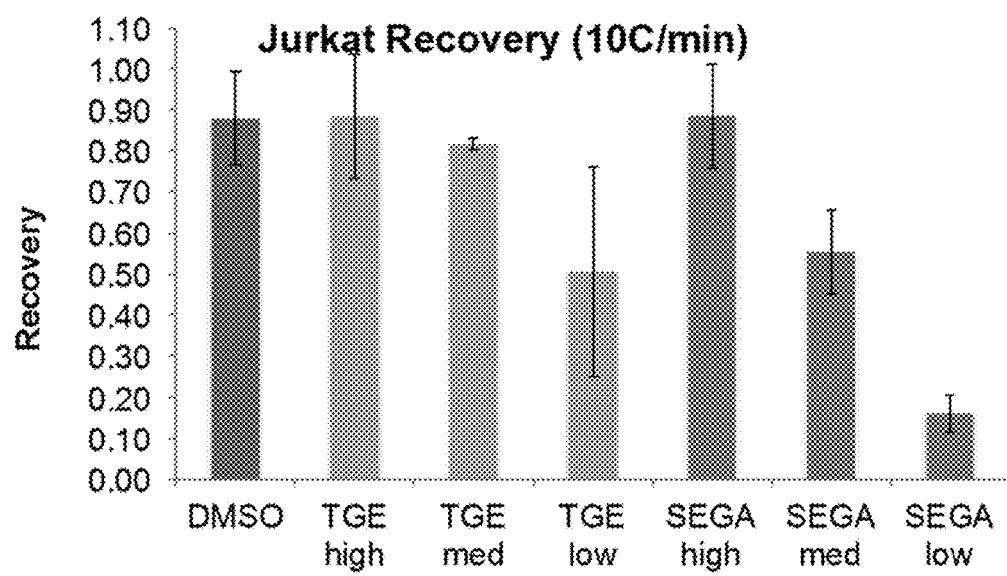

FIG. 10 shows that solutions tailored for Jurkats (TGE) outperformed solutions optimized for MSCS (SEGA). The solution tailored for use with Jurkat-cell-designed solution (TGE good, the TGE high bar in FIG. 10) outperformed all others in both viability and recovery. (FIGS. 10A and 10B).

Figure 16:
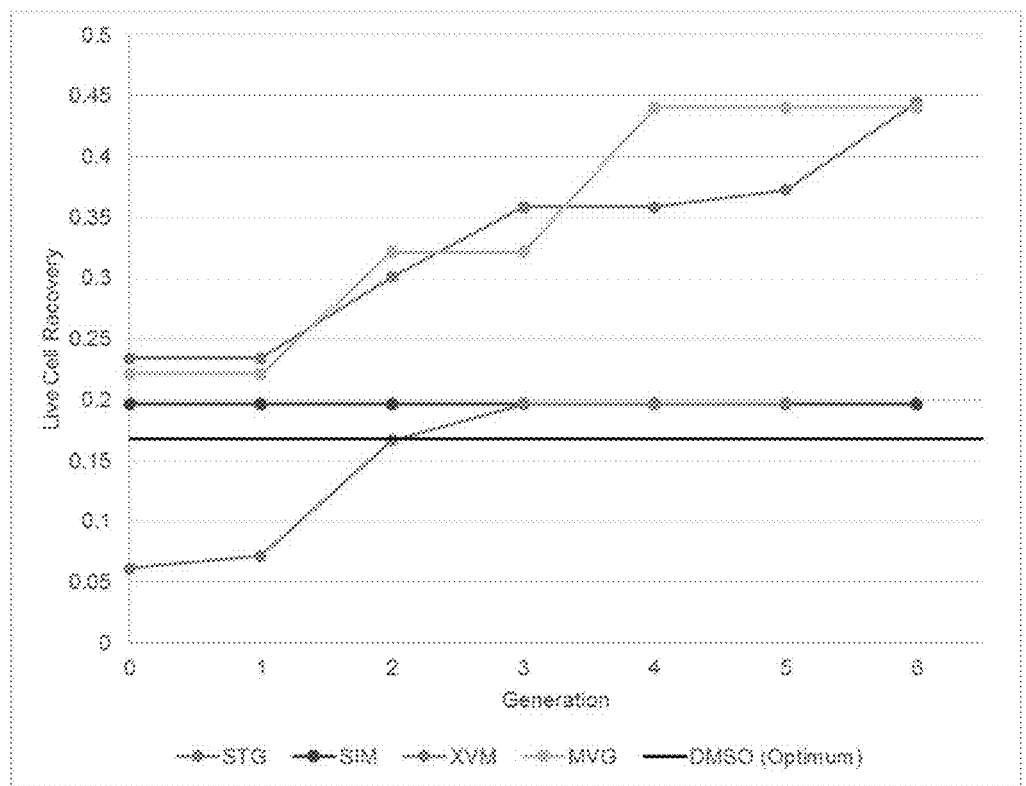
FIG. 16. Cumulative best recovery rate for test solution (STG, SIM, XVM, MVG) and average recovery for DMSO at its optimum cooling rate.
Figure 17:
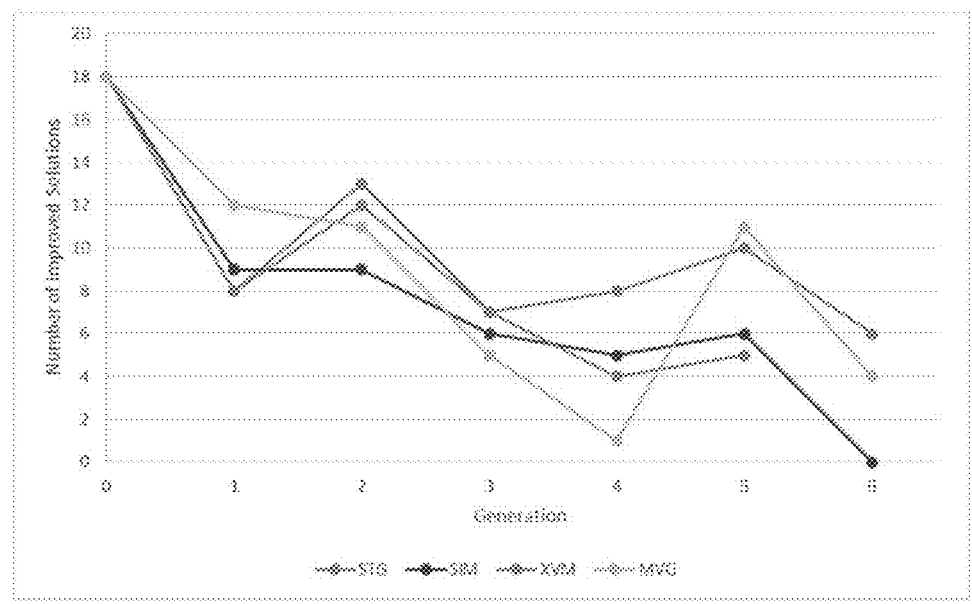
FIG. 17. Number of improved solutions per generation for each solution (STG, SIM, XVM, MVG).

FIG. 16 and FIG. 17 show data for alternative solutions tailored for use with Jurkat cells. Of the solution tested in FIG. 16 (Example 3), the solutions with the highest rate of recovery were the STG (sucrose, sorbitol, taurine, glycerol) and MVG (sucrose, mannitol, valine, glycerol) solutions. The SIM (sucrose, sorbitol, isoleucine, mannitol) and XVM (sucrose, xylitol, valine, mannitol) solutions had lower recovery rates that were still better than DMSO, however. The highest recovery rate at the end of each generation for each solution is shown in FIG. 16. XVM solutions trials were discontinued after generation five. Thus, six generations were tested for XVM, and seven were tested for STG, SIM, and MVG. In general, the highest recovery continued improving for each generation, and plateaued for all compositions except STG.

The number of compositions with improved recovery rates for each generation was counted for each solution and shown in FIG. 17. Each solution composition had a decreasing trend in the number of improved solutions as generation advanced.

Each of the STG solutions included sucrose, glycerol, sorbitol and taurine, whereas the MVG solutions included sucrose, glycerol, mannitol, and valine. Without wishing to be bound by any particular theory, one possibility is that different components of the composition could affect different proteins or different areas of the cell. One example of cell structure that could be affected differently by different osmolytes is the cell membrane. The cell membrane can be irreversibly damaged by volume changes and/or ice formation during cryopreservation, which can result in cell lysis. Both surface and internal membranes are potential areas of membrane cell injury regardless of cooling rate. Normal cells have a layer of water surrounding the cell surface, which helps maintain protein folding. During freezing, however, the concentration of liquid water decreases, which can lead to destabilization of proteins in the cell membrane. In the solutions used in this study, each component could differ in factors such as, for example, location (intracellular or extracellular), the macromolecules it stabilizes, and/or the surface area it stabilizes. The differences in the components could help with protecting multiple cellular structures, thus decreasing the cumulative damage to the cell.

For example, sugars can provide stabilization by replacing water surrounding membranes during dehydration. Larger sugars can provide better protection because they can insert between the phospholipid heads and create space for additional binding. Binding of sugars to membranes can increase the rigidity of the membrane, which can provide greater resistance to disruption. Cells can dehydrate at slow cooling rates. During thawing, changes in the protein environment can induce denaturing, but osmolytes including, for example, sugars can help with stabilization. This can reduce damage to membrane proteins and internal proteins.

Sugars are hydrophilic and cannot cross the plasma membrane without assistance from transporters. Disaccharides are more likely to be located outside the cell and, therefore, are in a better position to stabilize the outer membrane. Additionally, disaccharides can bind more of the membrane than monosaccharides because of their size.

Figure 11:
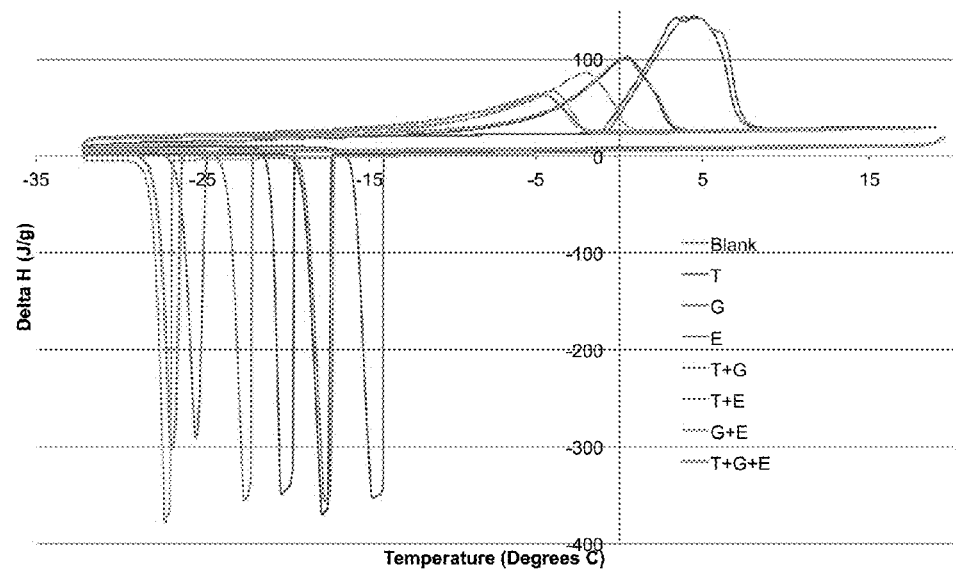
FIG. 11. Differential scanning calorimetry profile for trehalose-containing solutions (T), glycerol-containing solutions (G), and ectoine-containing solutions (E). Samples were frozen to −100° C. (temperature range is plotted only to −30° C.), and freezing point and melting point were reduced for solutions containing trehalose and glycerol. No glass transition was observed for any solution tested.

Next, samples of selected experimental solutions tested (no cells) were placed in sample pans and run down to −100° C. (only graphed to −30° C. in FIG. 11) using the same freezing protocol as used with cells in the controlled rate freezer. The freezing and warming profiles for the samples are shown in FIG. 11. The melting point and freezing point are reduced when there are more components in solution, which is an effect of increased concentration—higher osmolarity of the solution lowers the freezing point and melting point. However, osmolarity alone is not enough to affect cell recovery. A solution of PBS, which is roughly 300 mOsm does not result in high cell recovery. Also, there is no change in solution behavior at these solution concentrations below −30° C. There is no eutectic peak indicating that a glass transition occurred in any of the samples at these concentrations (not shown), and one would expect to see glass transition at around −80° C. if it existed. Because this physical change is absent, the mechanism of protection for these solutions may be biological.

Figure 12:
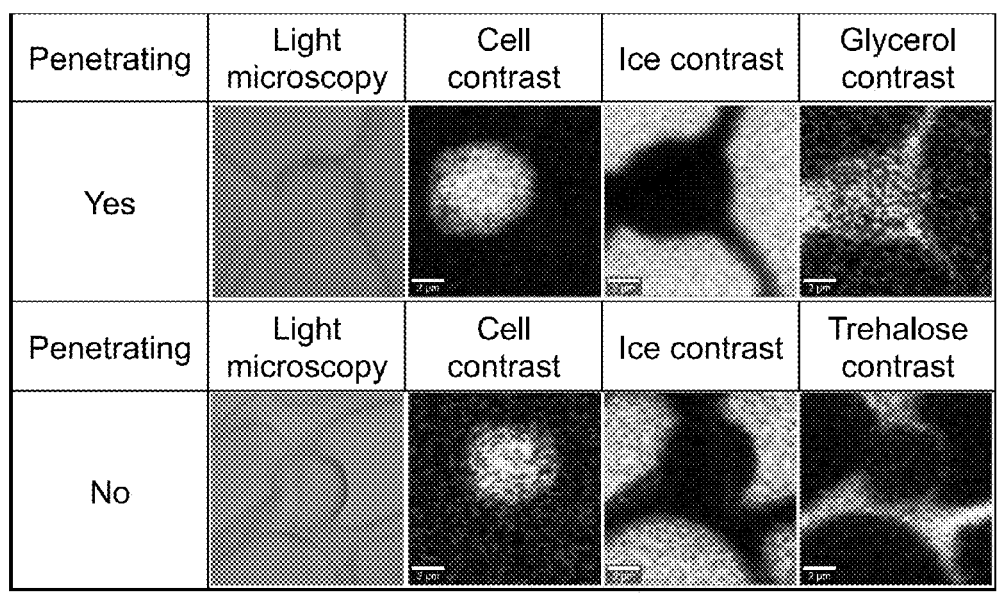
FIG. 12. Composite Raman images for penetrating and non-penetrating cryoprotectants. Glycerol was confirmed to be a penetrating cryoprotectant, as it is visible in both the cell space and the ice-void space. Trehalose, confirmed to be a non-penetrating cryoprotectant, is visible in the void space only outside the cell, as evidenced by the darker region in the trehalose image that corresponds to the area where cell contrast is visible in the cell image.

Raman microscopy data provides an indication of the location of action of each cryopreservative. The images in FIG. 12 show Jurkat cells frozen in either glycerol (penetrating) or trehalose (non-penetrating). Each contrast photo shows brighter colors (yellow and white) to indicate something is present, and darker colors (red and black) to indicate something is at lower concentrations or absent. Cell contrast shows that the cells have rounded morphology, and ice contrast shows the void between ice crystals, which includes both a cell and super cooled solution that has not crystallized. The glycerol contrast image shows that glycerol is present in the entire ice contrast void space, indicating that it is present both inside the cell and in the super cooled liquid surrounding the cell. The trehalose contrast image shows that trehalose is excluded from the cell and is only present in the super cooled liquid surrounding the cell. This suggests that trehalose does not penetrate the cell even at freezing temperatures and, thus, acts on the cell membrane.

These experiments were performed for most of the components described in the sections above both at room temperature and at freezing temperatures to assess whether penetration was temperature dependent. The results of these penetration studies are summarized in Table 9.

TABLE 9

| Category | Component | Penetration |
| --- | --- | --- |
| Sugar | Trehalose | Semi* |
|  | Fructose | Yes |
|  | Sucrose | Yes |
|  | Glucose | Yes |
| Sugar alcohols | Glycerol | Yes |
|  | Sorbitol | Yes |
|  | Ethylene glycol | Yes |
|  | Inositol | Yes |
|  | Xylitol | Yes |
|  | Mannitol | Yes |
| Amino Acids | Proline | Yes |
|  | Alanine | Yes |
|  | Valine | Yes |
| Other additives | Taurine | Yes |
|  | Ectoine | Yes |

*A small fraction of trehalose penetrates

Molecules excluded from the cell even at freezing temperatures must exert any biological protection on the cell membrane. Molecules that do not penetrate at room temperature and are found inside the cell at freezing temperatures may be improving cryopreservation by enabling pore formation in the cell membrane.

Figure 13:
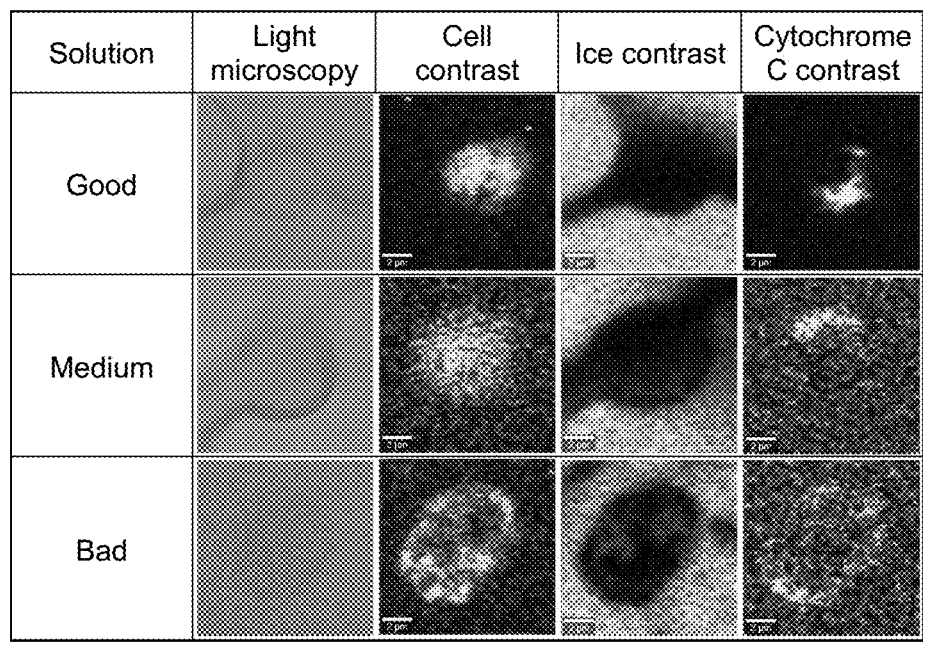
FIG. 13. Cytochrome c distribution for cells frozen with trehalose, glycerol, and ectoine (TGE) solutions. The same TGE-high (good), med, and low (bad) solutions tested in FIG. 9 and FIG. 10 were combined with cells and imaged for cytochrome c using Raman microscopy. In primarily cells frozen with the good/high solution, cytochrome c is concentrated within mitochondria, a Raman marker that can be used to confirm a cell is alive. In primarily dead cells frozen with the low/bad solution, cytochrome c has been released and is disperse, a Raman marker that can be used to confirm a cell is dead.
Figure 14:
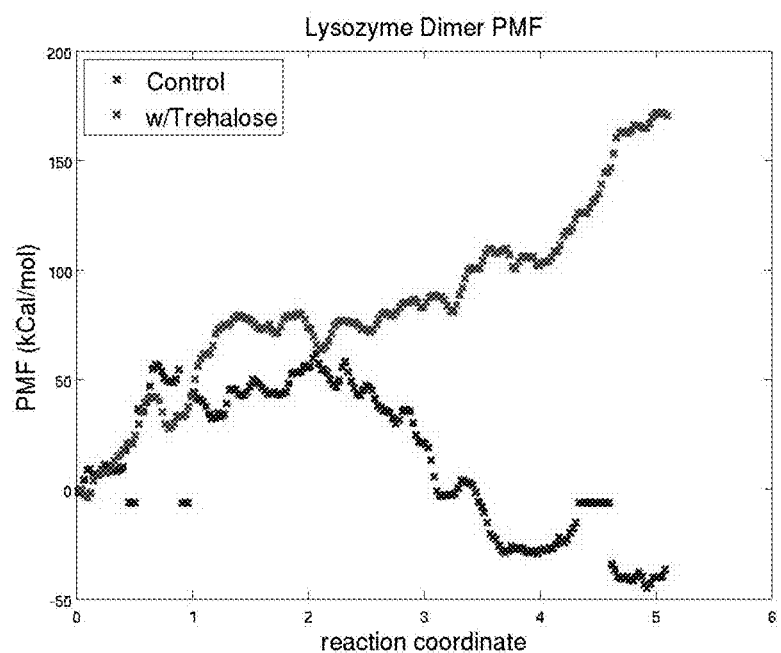
FIG. 14. Potential mean force distribution for lysozyme protein dimers. Potential mean force decreases as lysozyme proteins are moved closer together in the presence of trehalose (blue), while potential mean force increases as they are moved closer together for the control. This indicates trehalose stabilizes proteins in low energy conformations during dehydration/freezing.
Figure 15:
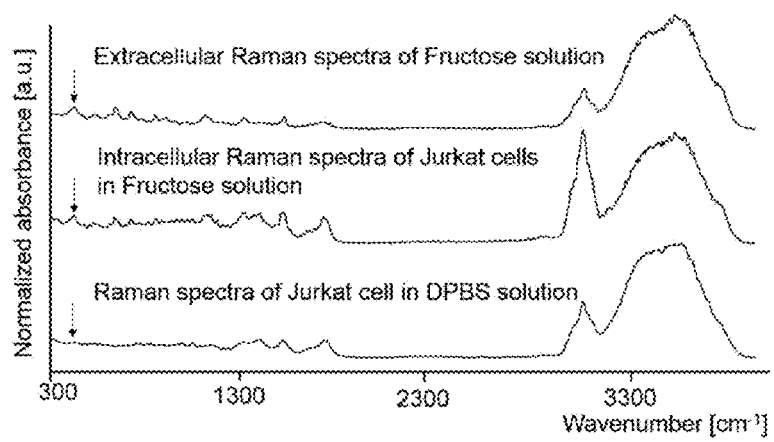
FIG. 15: Raman spectra of intracellular and extracellular compartments for cells in a solution containing fructose. Arrows indicate peaks associated with fructose.

This pore formation may be demonstrated to be non-lethal to cells by looking at the distribution of cytochrome c within the cell: a disperse distribution indicates that the cell is dead, while a concentrated pocket indicates that a cell is alive. An example of this distribution is shown in FIG. 13 for three example solutions, a good solution (300 mM trehalose, 5% glycerol, 0.01% ectoine) that has high live cell recovery (>90%), a medium solution (6 mM trehalose, 10% glycerol, and 0.5% ectoine; <70% live cell recovery), and a poor solution (30 mM trehalose, 0% glycerol, and 1% ectoine; <40% live cell recovery).

Molecular dynamics simulations measure potential mean force (PMF) in kcal/mol between two proteins in a one or two component solution at each point of the simulation for 100 ns. The proteins are brought closer together, which simulates dehydration. A reaction coordinate of 0 indicates that the proteins are right next to each other, while a reaction coordinate of 5 indicates that the proteins are as far apart as possible within the simulation. As one decreases the reaction coordinate, the PMF for proteins in trehalose decreases, indicating the arrangement is at an energy minimum for that system—i.e., is favorable. The opposite is true in the control. This means that adding trehalose to the system helps stabilize proteins as they dehydrate.

Figure 18:
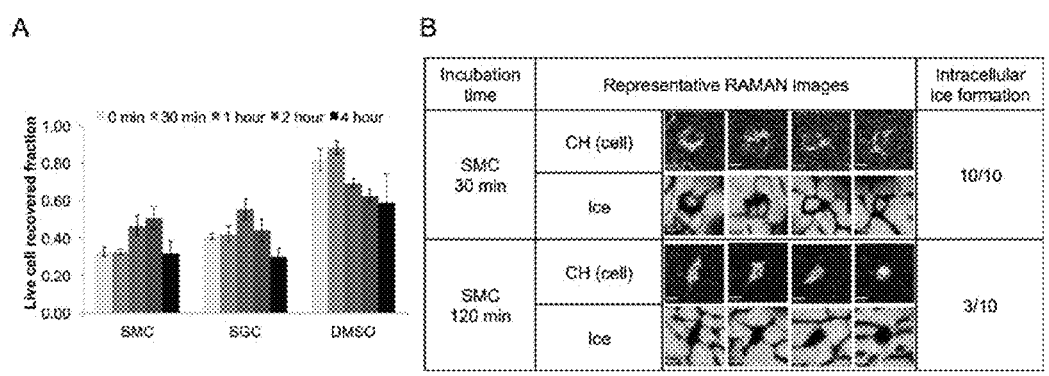
FIG. 18. Recovery reaches a maximum with appropriate incubation time for slow penetrating components (A) Fraction of live cells recovered for DMSO-free solutions SMC and SGC and DMSO solutions as a function of incubation time prior to freezing at 3° C./min; (B) Raman images obtained of MSCs frozen at 3° C./min in SMC solution after 30 and 120 minutes of incubation prior to freezing. Raman images are rendered for both —CH and ice.
Figure 19:
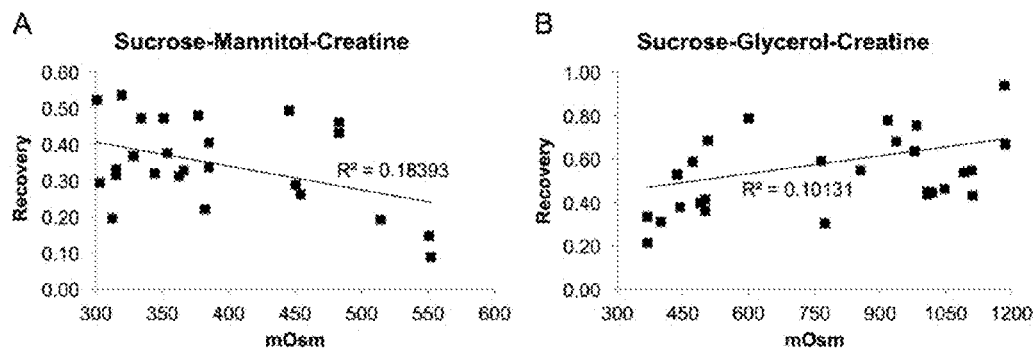
FIG. 19. Post thaw recovery of MSCs cryopreserved in SGC and SMC as a function of total solution osmolarity. Linear best fit is given with correlation coefficient. (A) Recovery of cells has slight negative correlation for different osmolarity sucrose-mannitol-creatine solutions. (B) Recovery of cells has slight positive correlation for different osmolarity sucrose-glycerol-creatine solutions.
Figure 20:
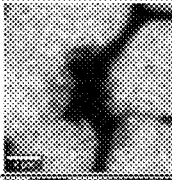
FIG. 20. Low temperature Raman microscopy of MSCs cryopreserved at 3° C./min in SGC with two different compositions. Images are rendered on ice, osmolyte mixture and —CH. The fraction of cells with ice is described for 10 cells measured.
Figure 20:
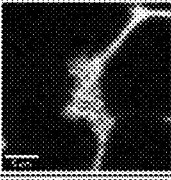
Figure 20:
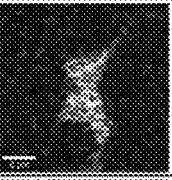
Figure 20:
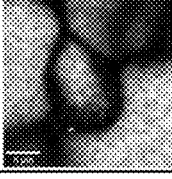
Figure 20:
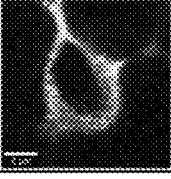
Figure 20:
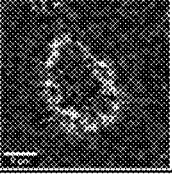

FIG. 18-20 show analysis of alternative compositions containing either sucrose, mannitol, and creatine (SMC) or sucrose, glycerol, and creatine (SGC). Incubation time influences cell responses to freezing, indicating that the cryoprotective solution require some time to permeate the cell and/or otherwise exert their cryoprotective effect. An SMC solution and an SGC solution (Table 14, Example 4) were incubated with cells at room temperature in NORMOSOL-R (Hospira, Inc., Lake Forest, Ill.) for 0 minutes, 30 minutes, one hour, two hours, or four hours before undergoing freezing at 3° C./min. Live cell recovery increased with incubation time and experienced a maximum at one hour for SGC samples, and two hours for SMC samples. (FIG. 18A).

MSCs were incubated for 30 minutes or 120 minutes in the SMC composition, frozen to −50° C., and imaged using low temperature Raman spectroscopy. Cells incubated for 30 minutes exhibited large internal ice crystals for 10/10 of the cells imaged. In contrast, cells incubated for 120 minutes exhibited ice in only 3/10 cells imaged. The formation of ice inside the cell is considered to be a damaging event. (FIG. 18B).

It is common for cryopreservation solutions to contain high concentrations of cryoprotective agents and therefore exhibit high solution osmolarity. For example, a 10% DMSO solution has an osmolarity of ~1400 mOsm. MSCs suspended in different combinations of sucrose, mannitol, and creatine (SMC) or sucrose, glycerol, and creatine (SGC) were frozen at 3° C./min, thawed, and the post-thaw recovery was measured. The post-thaw recovery of SGC and SMC were plotted as a function of total osmolarity for a range of different tested compositions (FIG. 19). For SMC solutions, the range of solution osmolarities is low (< 500 mOsm) and there is a weak negative correlation between osmolarity and post-thaw recovery of MSCs (FIG. 19(A)). In contrast, SGC solutions were evaluated over a higher range of osmolarities (< 1200 mOsm) and exhibited a weak positive correlation with the compositions tested (FIG. 19(B)). These weak correlations suggest that higher solution concentration does not necessarily correlate to higher levels of post-thaw recovery. Thus, osmolarity of the cryoprotective solution, alone, is not enough to predict cell recovery.

In order to understand differences in freezing response for different combinations of the same three osmolytes, freezing studies using two different compositions of SGC (SGC-A and SGC-B, Table 14) were repeated (FIG. 20). MSCs were frozen under the same conditions (total osmolarity and 3° C./min cooling rate) and imaged using low temperature Raman confocal microscopy. Cells frozen in SGC-B exhibited ice inside the cells for 10/10 cells imaged. In contrast, cells cryopreserved in SGC-A exhibited less intracellular ice formation (3/10 cells imaged), implying that 7/10 cells survived freezing. Post-thaw recovery trends (average±SEM, n=4) for cells frozen in SGC-A (0.82±0.07) and SGC-B (0.71±0.05) using conventional controlled rate freezing were consistent with the ice formation trends observed using Raman confocal microscopy—i.e., SGC-A had higher recovery and fewer cells with ice crystal formation than SGC-B.

Figure 21:
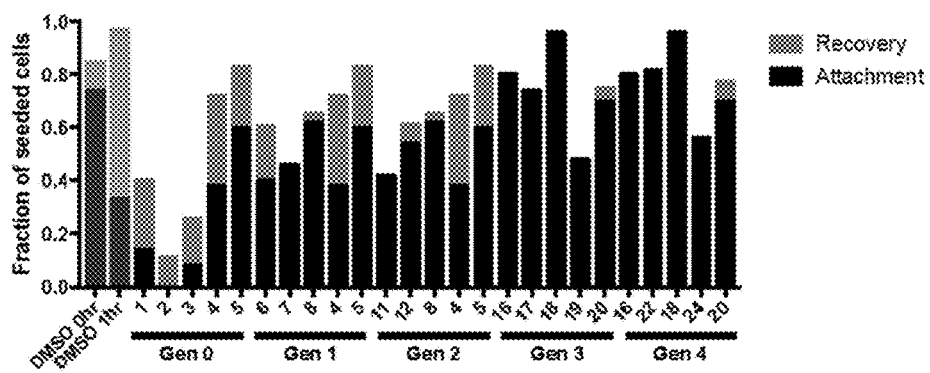
FIG. 21. Algorithm iterations and post-thaw characterization of optimized solutions. (A) Algorithm iterations increase both attachment and recovery of SGI solutions over five total generations. The analysis identified solutions having recovery and attachment characteristics comparable to DMSO frozen solutions. (B) Statistical replicates of solution iterations for SMC, SGC, and SGI tested in biological triplicate. Immediate post-thaw recovery, and two hours post-thaw attachment are reported for both experimentally and DMSO frozen cells. (C) DMSO recovery and attachment as a function of pre-freeze incubation time. Longer pre-freeze incubation at room temperature in DMSO solutions significantly reduces attachment of cells, but has limited effect on recovery.
Figure 21:
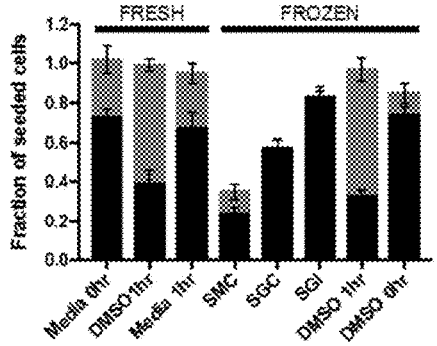
Figure 21:
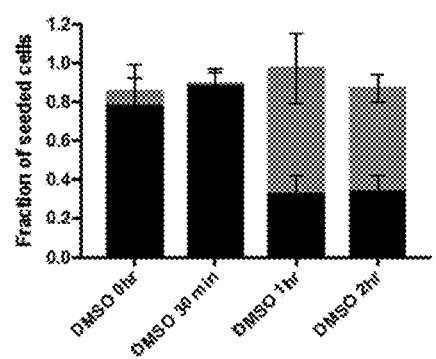
Figure 22:
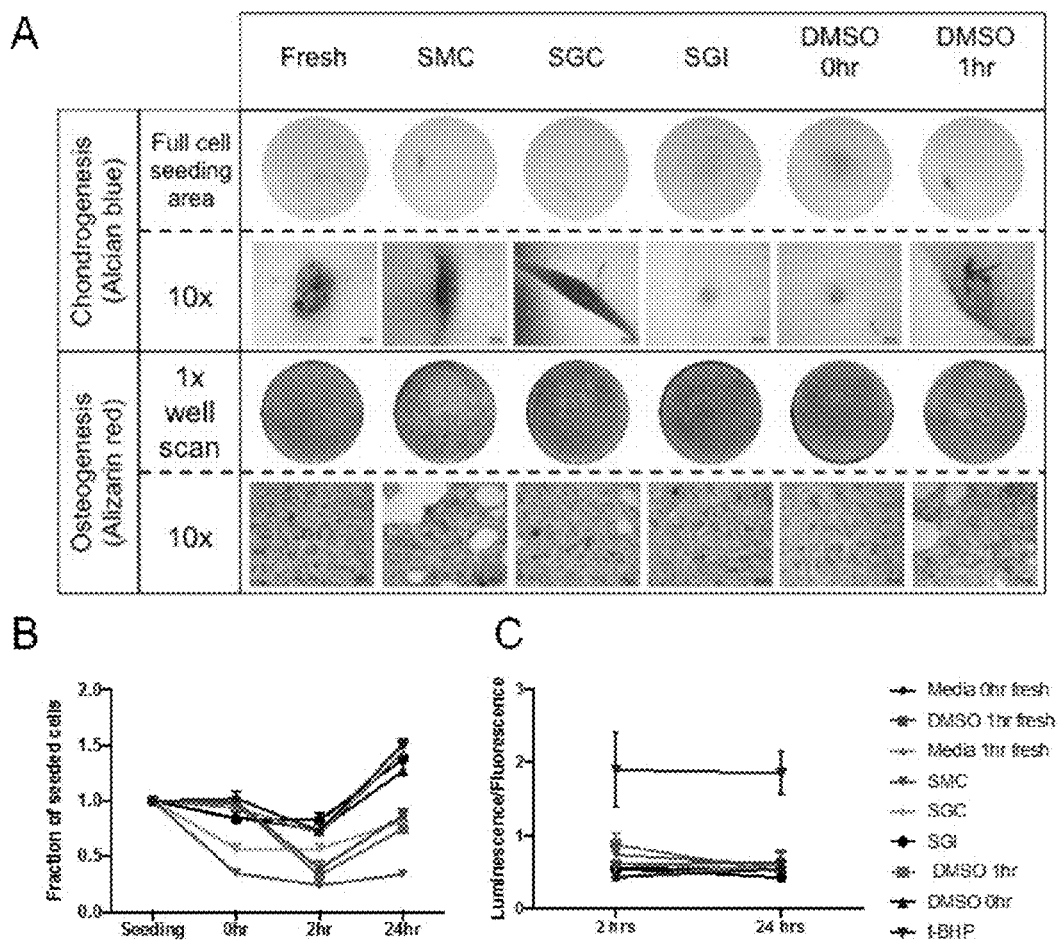
FIG. 22. Post-thaw characterization of MSC differentiation, proliferation, and senescence. (A) Multi-lineage differentiation potential is maintained in cells frozen in experimental solutions. There were no observable differences in chondrogenic and osteogenic differentiation and staining between experimental and fresh cells. (B) Proliferation rates were similar for SGI solutions compared to fresh and DMSO frozen cells (DMSO 0 hr) between two hours and 24 hours post-thaw. SMC and SGC solutions showed a slight reduction in proliferation rate for the same time range. (C) Beta-galactosidase expression as an indicator of senescence was not markedly different between any fresh, DMSO or experimental samples tested, and each of these were significantly lower than positive control t-BHP induced samples.
Figure 23:
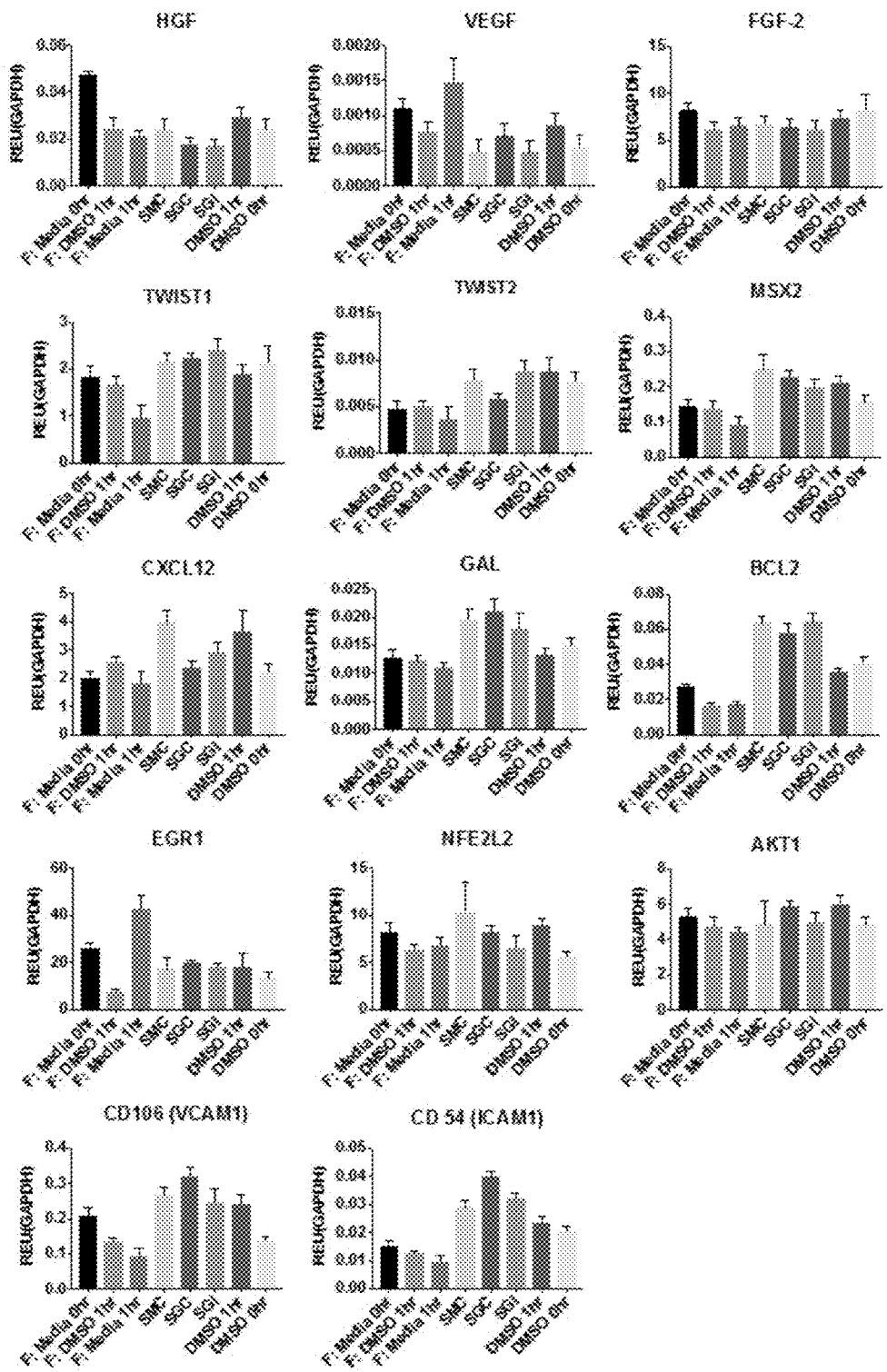
FIG. 23. Gene expression profiles for H9-MSCs immediately post-thaw. This panel included genes for growth factors, adhesion molecules, transcription factors, chemokines, and stress genes. Each reported value was compared to a GAPDH internal control.

FIG. 21-23 show post-thaw function and epigenetic changes in mesenchymal stromal cells cryopreserved using multicomponent osmolyte solutions. Different combinations of sugars, sugar alcohols, and small molecule additives were tested to identify the concentrations of components in solution which, when combined with cells, resulted in maximum cell attachment at two hours post-thaw. FIG. 21A shows a representative generational progression for a solution of sucrose/glycerol/isoleucine (SGI). Over multiple generations, the post-thaw recovery of live cells increases, and the percentage of those recovered cells that are able to attach to a surface also increases. This iterative process identified for three separate exemplary compositions that maximized cell attachment using different components in solution: SGC (0 mM sucrose, 1.25% glycerol, 2 mM creatine), SGI (30 mM sucrose, 5% glycerol, 7.5 mM isoleucine), and SMC (150 mM sucrose, 62.5 mM mannitol, 6.25 mM creatine).

MSCs frozen in these formulations were tested for attachment and recovery using statistical triplicates of biological replicates. FIG. 21B shows that samples frozen in experimental solutions have different attachment and recovery behavior. High performing combinations, such as SGI, display recovery and attachment that is not statistically different ($p>0.05$) from both fresh cells and samples frozen in DMSO without any further incubation (FIGS. 21B and 21C, 'DMSO 0 hr incubation'). Other experimental combinations including SGC and SMC displayed significantly lower recovery ($p<0.05$) compared to fresh samples, but had attachment values that approached their total recovery.

Incubating the cells in DMSO prior to freezing did not alter cell recovery, but significantly reduced the attachment of cells with a decreasing fraction of cells attaching with increasing time of DMSO exposure (FIG. 21C). Diminished cell attachment was observed for cells incubated with DMSO that do not undergo freezing (FIG. 21B).

MSCs frozen in osmolyte-based freezing solutions retain characteristic cell surface markers, proliferation, and osteochondral differentiation potential. Fresh MSCs, MSCs frozen in experimental solutions, and DMSO-frozen MSCs all showed normal expression of positive (>99% for CD73, CD90, CD105) and negative (<1% for CD45) surface markers. These surface marker expression characteristics are well within conventional thresholds for cell-surface phenotype expression, and show that freezing with DMSO and with experimental solutions does not change the expression of these markers significantly.

MSCs displayed normal multi-lineage differentiation in all samples, as shown in FIG. 22A. Micromass cultures treated with chondrogenic media all showed characteristic blue color after staining with Alcian blue, indicating that these cultures produced glycosaminoglycan (GAG) content consistent with chondrogenesis. Cell monolayers treated with osteogenic differentiation media showed characteristic red color after staining with Alizarin red, consistent with osteogenesis.

Analysis of proliferation (FIG. 22B) showed that proliferative capacity was maintained in SGI samples and was similar to both fresh and DMSO frozen samples, but was slightly reduced in SMC and SGC samples based on the reduced slope of their growth curves between two hours and 24 hours.

Senescence (FIG. 22C) did not vary significantly between samples. There were slight differences in senescence per cell at two hours, and these differences were reduced after 24 hours. All samples showed significantly lower senescence than positive control t-BHP treated cells.

Certain genes within select gene categories were analyzed using qRT-PCR. H9-MSCs subjected to different freezing approaches were assayed immediately post-thaw for the expression of genes related to trophic factor secretion such as HGF, VEGF, FGF2, CXCL12 (SDF-1α), mesodermal lineage markers TWIST1, TWIST2 (DERMO1), MSX2, the anti-apoptotic marker BCL2, surface markers for cell adhesion such as CD106 and CD54, the osmotic regulator marker GAL-1, and stress-response markers such as EGR1 and NFE2L2 (NRF2). The gene expression data for these genes is summarized in FIG. 23. These data show that the levels of HGF, an anti-scarring and anti-apoptotic factor, showed no differences between different freezing treatments, while fresh, non-frozen cells showed the highest level of HGF expression.

Different freezing conditions did not appear to have any marked effects in the expression of VEGF, the mitogen FGF2, the mesodermal genes MSX2 and TWIST1, the osmotic gene GAL or the anti-apoptotic gene BCL2. However, TWIST2 was elevated in almost all of the frozen groups (SMC, SGI, and DMSO freezing for one hour) except for SGC, which presented TWIST2 transcript levels comparable to fresh samples. Another notable change in gene expression was observed for CXCL12 in two treatment conditions (frozen SMC and DMSO 1 hr). Expression of mRNAs for MSC surface markers CD106/VCAM1 and CD54/ICAM1 was easily detected in H9-MSCs regardless of the anti-freeze solution. Assessment of stress-response genes such as EGR1 and NFE2L2 showed while expression of NFE2L2 did not differ among treatment groups, EGR1 levels were highly expressed in the Fresh Media 1 hr group and were significantly lower in the Fresh 1 hr DMSO-incubated samples and in all frozen groups.

The cryopreservation compositions can stabilize cellular proteins. Differential scanning calorimetry was used to characterize denaturation temperature ($T_m$) of lysozyme heating in single and multi-component osmolyte solution (Table 16, Example 6, below). The denaturation temperature of lysozyme increased in the presence of osmolytes. SSE-B had a slightly higher denaturation temperature than SSE-A, but the denaturation temperature of lysozyme in solutions containing a single osmolyte that is a component of the SSE compositions—i.e., sucrose, sorbitol and ectoine—is higher than the combination of the three osmolytes.

Figure 24:
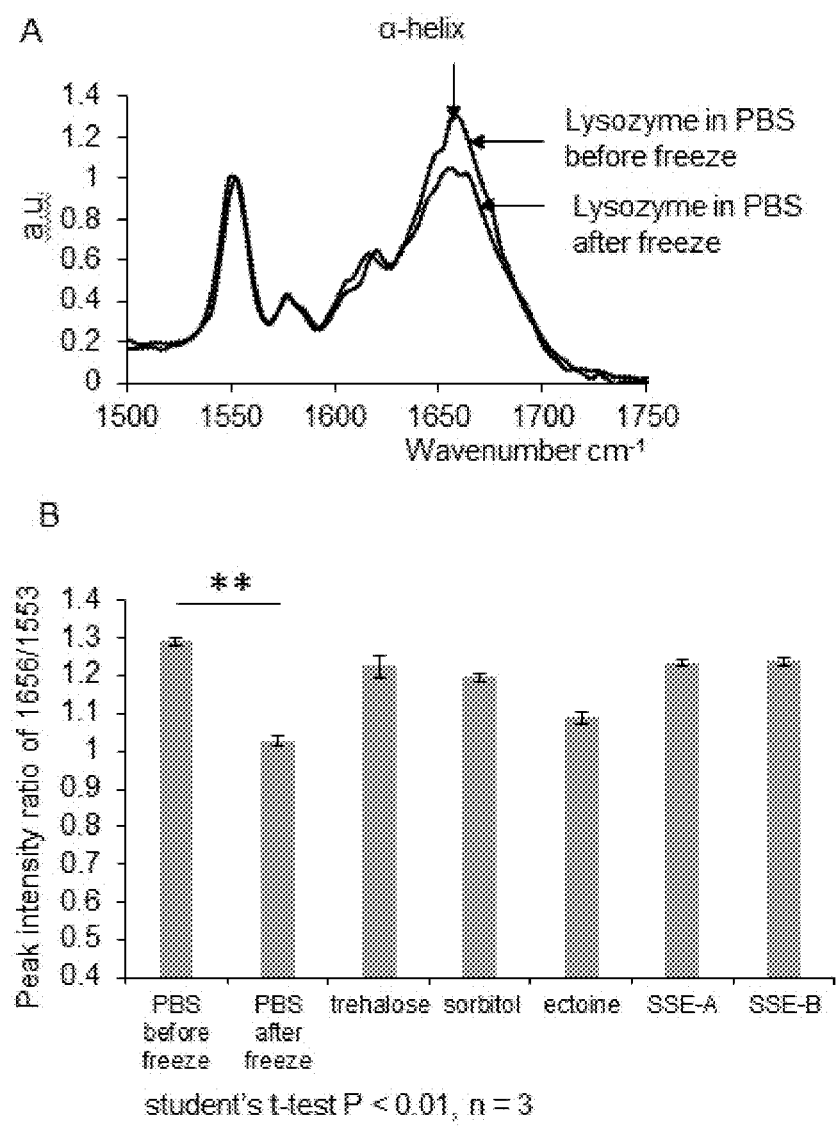
FIG. 24. Multicomponent solution effects on protein stability. (A) Raman spectra of lysozyme in DPBS solution at room temperature and after freezing at −50° C. respectively. Spectra were normalized to the trp group. (B) Peak intensity ratio of α-helix at 1655 $cm^{-1}$ to Trp group at 1553 $cm^{-1}$ for some of the solutions tested.

Low temperature Raman spectroscopy was used to study the secondary structure of lysozyme—as a model cellular protein—during freezing in single and multicomponent osmolyte solutions. Raman scattering is sensitive to changes in protein secondary structure, and the α-helix configuration of proteins can be detected. The spectra of lysozyme in DPBS at room temperature and −50° C. were normalized to the Raman peak at 1553 cm$^{-1}$ and are shown in FIG. 24A. The Raman peak at 1553 cm$^{-1}$ originates from trp group (tryptophan residues) and this group is considered free from feature changes and relatively stable as temperature changes, so it is appropriate for normalization purposes. The peak intensity of α-helix at 1655 cm$^{-1}$ significantly decreased for lysozyme in DPBS after freezing.

The peak intensity ratio of α-helix at 1655 cm$^{-1}$ to the trp group at 1553 cm$^{-1}$ was calculated and is shown in FIG. 24B. Lysozyme in DPBS before freezing and after freezing had the maximum and minimum value for the ratio of α-helix/Trp respectively. For all other osmolytes, this ratio fell between the maximum and minimum value, suggesting osmolytes were preventing the loss of lysozyme secondary structure to varying degrees. There were no significant differences in the secondary structure of lysozyme frozen in SSE-A and SSE-B suggesting that both solutions were effective in stabilizing lysozyme.

The sugar component of the cryopreservation composition can include any suitable monosaccharide or disaccharide. In some embodiments, the sugar component can include a disaccharide such as trehalose, sucrose, lactose, or maltose. In some embodiments, the sugar component can include a monosaccharide such as, for example, glucose or fructose, galactose. Also, the sugar component can include any combination of two or more sugars. In some embodiments, the composition can include a disaccharide. In certain embodiments, the sugar component can include trehalose or sucrose.

Generally, and regardless of the particular cell type with which the cryopreservation composition is used, the sugar component of the composition may be provided at a minimum concentration of at least 1 mM such as, for example, at least 2 mM, at least 3 mM, at least 4 mM, at least 5 mM, at least 6 mM, at least 7 mM, at least 8 mM, at least 9 mM, at least 10 mM, at least 20 mM, at least 30 mM, at least 40 mM, at least 50 mM, at least 100 mM, at least 150 mM, at least 200 mM, or at least 250 mM. The sugar component may be provided at a maximum concentration of no more than 500 mM such as, for example, no more than 475 mM, no more than 450 mM, no more than 425 mM, no more than 400 mM, no more than 375 mM, no more than 350 mM, no more than 325 mM, no more than 300 mM, no more than 275 mM, no more than 250 mM, no more than 225 mM, no more than 200 mM, no more than 175 mM, no more than 150 mM, no more than 125 mM, no more than 100 mM, no more than 90 mM, no more than 80 mM, no more than 70 mM, no more than 60 mM, or no more than 50 mM. The sugar component may be provided at a concentration within a range having endpoints defined by any minimum concentration listed above and any maximum concentration listed above that is greater than the minimum concentration. When more than one sugar is present in the composition, the concentration of the sugar component reflects the total concentration of all sugars in the composition. Thus, in some embodiments, the sugar component may be present at a concentration of from 0.1 mM to 300 mM such as, for example, from 100 mM to 300 mM.

The sugar alcohol component of the composition can include any suitable sugar alcohol. Exemplary suitable sugar alcohols include, for example, glycerol, sorbitol, ethylene glycol, inositol, xylitol, arabitol, erythritol, ribitol, or mannitol. In some embodiments, the sugar alcohol component can include any combination of two or more sugar alcohols. In certain embodiments, the sugar alcohol component can include glycerol, sorbitol, ethylene glycol, inositol, xylitol, or mannitol.

Generally, the sugar alcohol component of the composition may be provided at a minimum concentration of at least 0.1 M such as, for example, at least 0.2 M, at least 0.3 M, at least 0.4 M, at least 0.5 M, at least 0.6 M, at least 0.7 M, at least 0.8 M, at least 0.9 M, at least 1.0 M, at least 1.1 M, at least 1.2 M, at least 1.3 M, or at least 1.4 M. The sugar alcohol component may be provided at a maximum concentration of no more than 2.0 M such as, for example, no more than 1.9 M, no more than 1.8 M, no more than 1.7 M, no more than 1.6 M, no more than 1.5 M, no more than 1.4 M, no more than 1.3 M, no more than 1.0 M, no more than 0.90 M, no more than 0.8 M, no more than 0.7 M, no more than 0.6 M, or no more than 0.5 M. The sugar alcohol component may be provided at a concentration within a range having endpoints defined by any minimum concentration listed above and any maximum concentration listed above that is greater than the minimum concentration. When more than one sugar alcohol is present in the composition, the concentration of the sugar alcohol component reflects the total concentration of all sugar alcohols in the composition. Thus, in some embodiments, the sugar alcohol component may be present at a concentration of 0.1 M to 1.4 M. For example, certain embodiments can include glycerol at a concentration of 0.6 M to 1.4 M. Other particular embodiments can include an alternative sugar alcohol at a concentration of 0.1 M to 0.6 M.

Generally, the additive component can include an amino acid or other small molecule that contributes to the cryopreservation of cells within the solution. Exemplary small molecules are listed in Table 9. Additional small molecules that may be effective as an additive component include, for example, betaine, isoleucine, valine, dimethylglycine, ethylmethylglycine, histidine, n-acetylcysteine, an RGD peptide, or an antioxidant (e.g., a superoxide dismutase, glutathione, vitamin C, vitamin E, glutathione, lipoic acid, ubiquinol, uric acid, and/or alpha monothioglycerol).

The additive component of the composition may be provided at a minimum concentration of at least 1 mM such as, for example, at least 2 mM, at least 3 mM, at least 4 mM, at least 5 mM, at least 6 mM, at least 7 mM, at least 8 mM, at least 9 mM, at least 10 mM, at least 20 mM, at least 30 mM, at least 40 mM, at least 50 mM, at least 100 mM, at least 150 mM, at least 200 mM, or at least 250 mM. The amino acid component may be provided at a maximum concentration of no more than 300 mM such as, for example, no more than 275 mM, no more than 250 mM, no more than 225 mM, no more than 200 mM, no more than 175 mM, no more than 150 mM, no more than 125 mM, no more than 100 mM, no more than 90 mM, no more than 80 mM, no more than 70 mM, no more than 60 mM, or no more than 50 mM. The amino acid component may be provided at a concentration within a range having endpoints defined by any minimum concentration listed above and any maximum concentration listed above that is greater than the minimum concentration. When more than one amino acid is present in the composition, the concentration of the amino acid component reflects the total concentration of all amino acids in the composition. Thus, in some embodiments, the additive component may be present at a concentration of 0.1 mM to 300 mM such as, for example, 3 mM to 150 mM.

Generally, the composition can be free of DMSO or at least substantially free of DMSO. As used herein, "free of DMSO" refers to a composition that contains no more than trace amounts of DMSO and may be absolutely free of DMSO. As used herein, "at least substantially free of DMSO" refers to a solution that contains a level of DMSO that provides no greater cryopreservation than the remaining components of the solution—i.e., an amount of DMSO that is inconsequential to the functionality of the solution.

Thus, in one aspect, this disclosure describes a cryopreservative composition. Generally, the cryopreservative composition includes a sugar component and a sugar alcohol component, as set forth in more detail above. In some embodiments, the at least a portion of the sugar component may not necessarily penetrate the cell membrane and, therefore, act on the out surface of the cell. In such cases, the sugar component can include trehalose. In some embodiments, the cryopreservative composition can further include an additive component. Generally, the cryopreservative composition possesses an amount of DMSO that provides no more cryoprotection than the remaining components of the composition without the DMSO.

In some cases, the cryopreservative composition further includes a cell. Initially, the cell may be added to the cryopreservative composition prior to being cryopreserved and stored. In other cases, the cell may be being stored as a component of a frozen cryopreservative composition. In still other cases, the cell may be a viable cell recoverable from a thawed cryopreservative composition. As used herein, a "viable" cell includes a cell that remains living—under culture conditions suitable for the cell—after having been stored frozen in a cryoprotective solution, stored below 0° C., then thawed and removed from the cryoprotective composition.

Thus, this disclosure also describes a method of cryopreserving and storing a cell. Generally, the method includes adding a cell to any embodiment of the cryoprotective composition described above, freezing the composition, storing the frozen composition at a temperature below 0° C., thawing the composition, removing the cell from the thawed composition, and culturing the cell under conditions effective for the cell to remain viable.

In some embodiments, the method can include controlled rates of cooling and/or controlled rates of re-warming.

In certain embodiments the composition may be frozen using a protocol that reduces the extent and/or likelihood that stochastic ice forms in the cells as they are frozen within the cryoprotective composition. In such embodiments, freezing the cells can include one or more cycles of cooling, re-warming, and re-cooling the cryoprotective composition to which cells have been added. For example, the freezing protocol can include one or more cycles of cooling (at an exemplary rate of −50° C./minute) and re-warming (at an exemplary rate of +15° C./minute). Thus a complete freezing protocol can include, for example, cooling a specimen (cells and cryopreservative composition) at a rate of −10° C. per minute until the temperature reaches 0° C., then holding the temperature at 0° C. for 15 minutes. The specimen can then be cooled at a rate of −1° C. per minute until the specimen reaches a temperature of −8° C., followed by one or more cycles of more rapid cooling and re-warming. For example, the specimen may be cooled at a rate of −50° C. per minute until the specimen reaches a temperature of −45° C., then warmed at a rate of +15° C. per minute until the specimen reaches a temperature of −12° C., before being cooled to an appropriate storage temperature (e.g., −100° C.). The final cooling step may involve cooling the specimen at a rate of, for example, −0.5° C. per minute, −1° C. per minute, −3° C. per minute, −5° C. per minute, or −10° C. per minute, depending, at least in part, on the constituents of the cryopreservative composition and cells in the specimen.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Cell Culture

The lymphoblastoid cells used in this study (Jurkat cells, ATCC, TIB-1522) were cultured in medium composed of high glucose RPMI 1640 (Life Technologies, Carlsbad, Calif.), and 10% FBS (Qualified, Life Technologies, Carlsbad, Calif.). Jurkat cells were cultured to maintain cell density within $1\times10^5$ to $3\times10^6$ cells/mL. The mesenchymal stem cells (MSCs) used in this study were derived from H9 embryonic stem cells as previously described (Trevedi et al., 2008, *Exp Hematol* 36:350-359). MSC medium was composed of αMEM base with glutamine (powder, Life Technologies, Carlsbad, Calif.), 10% FBS (Qualified, Life Technologies, Carlsbad, Calif.), and 1% non-essential amino acids (Life Technologies, Carlsbad, Calif.). Tissue culture flasks were coated with 0.1% porcine gelatin (Sigma-Aldrich, St. Louis, Mo.) for a minimum of two hours before cell seeding. MSCs were seeded in gelatin-coated flasks at a density of approximately 2500 cells/cm². Cells were split or used for experiments when they reached approximately 70-80% confluence and were used for experiments only from passages 8 to 12.

Algorithm

The DE algorithm used in this study was developed from strategy 2 (DE/local-to-best/1, which balances robustness and convergence) by Storn and Price (1997, *J Global Optim* 11(4):341-359) and was coded in MATLAB with discrete parameter values. The DE algorithm utilizes stochastic direct search and independently perturbs population vectors to identify a global maximum within the user-defined parameter space. Briefly, the DE algorithm randomly generates an initial population (generation 0) that spans the entire parameter space. This population is composed of a given number of solutions expressed as vectors (a set of numbers), and the number of different solution components being tested defines how many slots the population vectors have. Experimentally, these vectors correspond either to the different levels of solute in a solution or to different cooling rates (Table 10). Cells are frozen at DE algorithm dictated cooling rates with solutions made from these vector specifications, and the resulting experimental recoveries are iterated back into the DE algorithm.

The DE algorithm utilizes this experimental information to modify the existing population vectors, and predicts solutions that may result in more favorable recovery. Briefly, the algorithm mutates existing vectors to generate new test vectors, and performs head to head comparisons of the resulting experimental recovery of each of the population slots. The best value from this comparison (either the original or the new mutant vector) is stored in an emergent population. This mutation/comparison process is repeated for all subsequent generations (FIG. 1) and results in an emergent population that changes less and less as the algorithm converges. The final emergent population contains a set of solutions that have all been independently optimized using stochastic direct search and contains the best possible compositions for freezing cells within the defined parameter space. Convergence can be measured by observing an increase in cumulative best member recovery, a decrease in the number of improved solutions within the emergent population after each generation, or by the generational average, which captures both these metrics.

For these experiments, the generation size was set to either 18 or 27, the crossover set to 1, and the weight set to 0.85. The concentration of each component was allowed to vary discretely between 0 and the maximums that were identified from the literature or dictated by solubility limits. The concentrations used for each discrete level are listed in Table 10.

TABLE 10

Concentration levels and cooling rates used for each component in the DE algorithm

| Component | Level 0 (0) | Level 1 (1/100) | Level 2 (1/50) | Level 3 (1/10) | Level 4 (1/2) | Level 5 (1) |
|---|---|---|---|---|---|---|
| Trehalose | 0 | 3 mM | 6 mM | 30 mM | 150 mM | 300 mM |
| Glycerol (v/v %) | 0 | 13.7 mM 0.1% | 27.4 mM 0.2% | 137 mM 1% | 685 mM 5% | 1370 mM 10% |
| Ectoine (w/v %) | 0 | 0.7 mM 0.01% | 1.4 mM 0.02% | 7 mM 0.1% | 35 mM 0.5% | 70 mM 1% |
| Sucrose | 0 | 3 mM | 6 mM | 30 mM | 150 mM | 300 mM |
| Ethylene glycol | 0 | 3 mM | 6 mM | 30 mM | 150 mM | 300 mM |
| Alanine | 0 | 3 mM | 6 mM | 30 mM | 150 mM | 300 mM |
| Taurine | 0 | 0.5 mM | 1 mM | 5 mM | 25 mM | 50 mM |
| Cooling rate (different scaling) | 0 | 0.5° C./min | 1° C./min | 3° C./min | 5° C./min | 10° C./min |

High throughput 96-well Plate Freezing

In both screening and DE algorithm experiments, cells were frozen in 96-well plates to limit the number of cells and volumes of reagent necessary, and to increase the number of samples that could be tested at one time. Solutions were made at 2× their final concentration in distilled H₂O (diH₂O). Cells were concentrated in NORMOSOL-R (Hospira, Inc., Lake Forest, Ill.) and combined 1:1 with 2× solutions in clear bottom black 96-well plates (Corning, Corning, N.Y.) to produce a 1× concentration of cryoprotectant solution (total volume 50 µL). As a control, wells of 10% DMSO solution were also included on each plate to normalize results between all experiments. All samples were run in triplicate wells on each plate. Plates were sealed with molded silicone round well covers (Laboratory Supply Distributers, Millville, N.J.) to prevent desiccation during freezing and storage. Plates were placed in a rack in a controlled rate freezer, and frozen using the profile below:

1. Starting temp 20° C.
2. −10° C. per minute to 0° C.
3. Hold at 0° C. for 15 min
4. −1° C./min to −8° C.
5. −50° C./min to −45° C.
6. +15° C./min to −12° C.
7. −0.5, −1, −3, −5, or −10° C./min to −100° C. (as dictated by the DE algorithm)

The rapid cooling and re-warming in steps 5 and 6 are included to promote ice crystal nucleation outside the cell before slow cooling proceeds, discouraging stochastic ice formation within cells.

Vial Freezing

Freezing of cells in vials was performed to compare the post thaw recovery obtained in 96-well plates (50 µL) to that observed in conventional cryovials (1 ml). Briefly, solutions were prepared at 2× the final freezing concentration and added stepwise to cells in NORMOSOL-R (Hospira, Inc., Lake Forest, Ill.) at a 1:1 final volume ratio in a 1.8 mL Nalgene™ CryoTube vials (Nunc, Thermo Scientific, Waltham, Mass.). Vials were moved to the freezer immediately and were frozen using the same protocol as 96-well plates.

Thawing

Both 96-well plate and vial samples were thawed using a 37° C. water bath. Vials were submerged in a 37° C. bath (to just under cap level) and agitated until only a small ice crystal was present.

Plates were thawed using a 37° C. water bath as well. Briefly, plates were submerged to half their height and agitated for 1 minute. At t=1 minute, they were removed from the bath and the silicone cover was removed to observe samples as they thawed. The plates were returned to the 37° C. water bath and submerged to half their height again. When opaque samples became transparent (approximately 1 minute after being returned to the water bath) the plates were removed for immediate addition of viability dye. Thermocouple probe analysis of the freezing and thawing rate in different wells of a 96 well plate showed no significant difference existed in temperature profiles of the wells tested in experiments.

Viability Assessment

The viability of all cells was assessed before freezing using fluorescent acridine orange/propidium iodide (AO/PI) using the method previously described (Pollock et al., 2015, *Cytotherapy* 17(1):38-45). Briefly, AO/PI was added to cell samples, and live and dead cells were enumerated using a hemocytometer (a minimum of 200 cells were counted). This method was also used to measure the viability and recovery of vial samples immediately after thawing. Viability was determined by dividing the number of live cells by the number of total cells. Recovery was determined by dividing the number of live cells post thaw by the number of live cells seeded pre-freeze.

After 96 well plates were thawed, calcein-acetoxymethyl (AM)/propidium iodide was added to each well and the wells were covered from light and placed in a 37° C. incubator for 30 minutes to allow the live cells to cleave calcein-AM. The plates were then analyzed for fluorescence on a plate reader. Raw fluorescence values were used to calculate the number of live and dead cells present in each well by correlating to a control curve of unfrozen cells. The live cell recovery was calculated by dividing the number of live cells present in thawed samples (calcein-AM plate reader fluorescence) by the number of live cells seeded pre-freeze (AO/PI counts). To normalize results between different plates and different cooling rates, these raw recoveries were divided by a control well containing 10% DMSO on the same plate, then multiplied by a standard DMSO recovery at each cooling rate to give the 'scaled raw recovery'. Example calculation:

$$\frac{\text{Raw recovery}}{\text{DMSO plate recovery}} * DMSO \text{ standard recovery} =$$

$$\frac{0.2}{0.15} * 0.16 = 0.21 = \text{scaled raw recovery}$$

Statistics

Error bars represent standard deviations of a minimum of 9 sample measurements, taken from experiments performed in batches of 3-6 over a minimum of 3 different days. Statistical significance was determined using a students t-test, with a significance level of $p=0.05$.

Example 2

Cell Culture

A lymphocyte cell model (Jurkats, ATCC) was cultured in high glucose RPMI 1640 (Gibco) in a 37° C. incubator at 5% $CO_2$. Cell concentrations were kept between $1 \times 10^5$ and $3 \times 10^6$ cells/mL, and cells were used for experiments or underwent media changes every 3-4 days.

Liquid-Handling Robot High Throughput Solution Screening

High throughput factorial screening experiments were performed on a Biomek Beckman FX 96 liquid handling robot. Briefly, 12.5 µl of an array of additives were transferred to nine 96-well plates containing 12.5 µl of different sugar alcohols. Cells (25 µl) diluted in either a sugar (in a solution of NORMOSOL-R; Hospira, Inc., Lake Forest, Ill.) or a NORMOSOL-R blank solution were transferred to these nine plates to give a final volume of 50 µl in each well. Cells suspended in 10% DMSO in media were also included as a row of each plate to serve as normalization wells for plate-to-plate comparison.

When all plate volume transfers were complete, silicone plate covers were used to seal each plate, and plates were transferred to a controlled rate freezer (Kryo 10 Series III, Planer PLC, Middlesex, United Kingdom) and frozen at cooling rates ranging from 1° C./min to 10° C./min. The concentrations of components present in solution are listed in Table 11, and were selected based on values described in literature or solubility limits. Component concentrations were 0 if not listed in a solution.

TABLE 11

| Solution component | Concentration |
|---|---|
| Sucrose | 300 mM |
| Trehalose | 300 mM |

TABLE 11-continued

| Solution component | Concentration |
|---|---|
| Glycerol | 300 mM |
| Sorbitol | 300 mM |
| L-arabitol | 300 mM |
| Inositol | 75 mM |
| Erythritol | 100 mM |
| Xylitol | 400 mM |
| Mannitol | 250 mM |
| Ribitol | 75 mM |
| Proline | 300 mM |
| Alanine | 300 mM |
| Isoleucine | 75 mM |
| Creatine | 25 mM |
| Valine | 100 mM |
| Taurine | 50 mM |
| Ectoine | 70 mM |

Concentration

Combinations were iterated experimentally through a differential evolution algorithm described in detail in Pollock et al. (Algorithm-driven optimization of cryopreservation protocols. Submitted to *Tissue Eng Reg Med*, October 2015). Briefly, the algorithm utilizes experimental input to predict component concentrations that will result in higher recovery. After several iterations, a solution composition can be identified that maximizes cell recovery within the concentration bounds provided.

Positive/Negative Solution Screening

In order to determine if all solution components identified by the algorithm are necessary to produce maximal recovery, 96-well plate freezing studies were performed with and without components at their algorithm optimized concentrations. Additional studies with each individual component in solution at a concentration that realizes the optimized solution osmolarity were also performed to determine whether osmolarity or solution composition was the critical factor in determining cell survival.

Scale Up Vial Freezing Studies

Vial freezes were performed to confirm that results from 96-well studies were scalable to larger, more clinically relevant volumes. Briefly, cells suspended in NORMO-SOL-R (Hospira, Inc., Lake Forest, Ill.) were combined stepwise with an equal volume of 2× experimental freezing solutions to give a final volume of 1 mL. Vials were capped and cooled in a controlled rate freezer using the same freezing protocols described above.

Thawing

Both vials and 96-well plates were thawed in a 37° C. water bath. Vials were submerged halfway and agitated until only a miniscule ice pellet remained. Cells were assessed for viability immediately post thaw, and the remaining volume was suspended in fresh pre-warmed media and centrifuged. After pelleting, the cells were re-suspended in fresh media and cultured for 48 hours in a 37° C. incubator at 5% $CO_2$ to assess post-thaw proliferation.

Plate thawing was performed by submerging 96-well plates halfway in a 37° C. water bath. After 1 min, silicone plate covers were removed to observe the thawing behavior of the wells. Plates were replaced in the water bath for an additional 30 seconds to 1 minute until opaque frozen samples became transparent. Plates were then immediately processed for viability.

Viability and Functionality

Cells were assessed for viability at the conclusion of each experiment. Both pre-freeze counts, and all post-thaw vial counts (0 hr and 48 hr) were performed using acridine orange/propidium iodide (AO/PI). Briefly, cells were combined with AO/PI, loaded into a hemocytometer, and counted manually using a fluorescent microscope. A minimum of 200 total cells were counted for each sample.

Plate samples were also assessed for viability using fluorescence. Briefly, a solution of calcein-AM/propidium iodide was prepared and a volume of 50 μl was added to each sample well of experimental 96-well plates, producing a 1:1 dilution. Plates were protected from light and placed in an incubator for 30 minutes to allow for calcein-AM digestion. A fluorescent plate reader (Synergy HT, BioTek Instruments, Inc., Winooski, Vt.) was used to determine the fluorescence in each well, which was correlated to live and dead cell counts using a control curve.

Viability was calculated for all samples by dividing the number of live cells by the number of total cells. Recovery was calculated directly by dividing the number of live cells post thaw by the number of live cells pre-freeze. Recovery for 96-well plate samples was further normalized; each experimental sample recovery was divided by the DMSO recovery on the same plate, and then multiplied by the standard DMSO recovery for the cooling rate of each experiment.

Differential Scanning Calorimetry

Differential scanning calorimetry was performed on a Perkin-Elmer Pyris 1 according to the manufacturer's instructions. The solutions tested contained trehalose, glycerol, and/or ectoine in the concentrations shown in Table 12.

TABLE 12

| Solution name | Trehalose | Glycerol | Ectoine |
|---|---|---|---|
| TGE | 300 mM | 5% | 0.01% |
| TG | 300 mM | 5% | 0 |
| TE | 300 mM | 0 | 0.01% |
| GE | 0 | 5% | 0.01% |
| T | 300 mM | 0 | 0 |
| G | 0 | 5% | 0 |
| E | 0 | 0 | 0.01% |
| Blank | 0 | 0 | 0 |

Raman Microscopy

Confocal Raman Microspectroscopy (CRM) measurements are conducted using Witec Confocal Raman Microscope System Alpha 300R (WITec, Wissenschaftliche Instrumente and Technologie GmbH, Ulm, Germany) with UHTS300 spectrometer and DV401 CCD detector. A wavelength of 532 nm Nd:YAG laser and 10 mW of power is used as excitation source. The laser is transferred to the microscopy in a singer fiber. A 100× air objective (NA 0.90; Nikon Instruments, Melville, N.Y.) is used for focusing the 532 nm excitation laser to the sample. Data collection and analysis are performed by Windows-based WitecControl_1.38 software.

Molecular Dynamics Simulations

Gromacs molecular dynamics software (Berendsen et al., 1995, *Comp Phys Comm* 91:43-56; Páll et al., 2015, *Proc EASC 2015 LNCS* 8759:3-27) with the Martini coarse grain force field was used to perform molecular dynamics simulations. A lysozyme dimer (3VFX from the protein data bank) was placed in a first solution containing coarse-grain water and also in a second solution containing water and trehalose. The dimer was oriented with respect to the x-axis. A pulling simulation was conducted, moving the two lysozymes apart from their initial positions to a separation of 5 nm between their centers of mass. From this pulling simulation, the positions at every distance were taken and an individual molecular dynamics simulation was conducted at each distance using a potential (spring) to fix the monomers at the specified distance. From the simulation outputs at every distance, a weighted histogram analysis method was used to construct a free energy curve.

using a control rate freezer, set to cooling rates of 0.5° C./min, 1° C./min, 3° C./min, 5° C./min, or 10° C./min. After freezing protocol, plates were stored in a deep freezer until thawing.

TABLE 13

| Solution name | Sugar | Polyol | | | | Amino Acid | | |
|---|---|---|---|---|---|---|---|---|
| | Sucrose | Glycerol | Mannitol | Sorbitol | Xylitol | Ile | Tau | Val |
| STG | 300 mM | 10% | | 300 mM | | | 50 mM | |
| SIM | 300 mM | | 250 mM | 150 mM | | 75 mM | | |
| XVM | 300 mM | | 250 mM | | 400 mM | | | 100 mM |
| MVG | 300 mM | 10% | 250 mM | | | | | 100 mM |

Statistics

To assess the importance of the four explanatory variables of interest (Sugar, Rate, Additive and Alcohol), without neglecting the variation between each batch and between each plate within the batches, we sought to find the best Linear Mixed Effects (LME) model. With $y_i$ the i'th outcome of the response, $X_i$ the corresponding values of the covariates, the LME model is defined as $$y_i = X_i\beta + Z_i\gamma + \epsilon_i,$$

where $\beta$ is a vector with the fixed effects, $\gamma$ is a vector with random effects normally distributed with mean 0, and $Z_i$ is the design matrix for the random effects. $\epsilon_i$ is the error term, normally distributed with mean 0.

To select the most fitting model, we performed backward elimination based on the Bayesian Information Criterion (BIC) starting with a model that includes all variables and second order interactions. Furthermore, we included two random variables, one to catch the effect of the batch, and one to catch the effect of each plate within the batch—i.e., the full model is:

$$y_i = x_{i,Sugar}\beta_{Sugar} + x_{i,Rate}\beta_{Rate} + x_{i,Alcohol}\beta_{Alcohol} + x_{i,Additive}\beta_{Additive} + x_{i,Sugar \times Rate}\beta_{Sugar \times Rate} + x_{i,Sugar \times Additive}\beta_{Sugar \times Additive} + x_{i,Sugar \times Alcohol}\beta_{Sugar \times Alcohol} + x_{i,Rate \times Additive}\beta_{Rate \times Additive} + x_{i,Rate \times Alcohol}\beta_{Rate \times Alcohol} + x_{i,Additive \times Alcohol}\beta_{Additive \times Alcohol} + z_{i,Batch}\gamma_{batch} + z_{i,Plate}\gamma_{Plate} + \epsilon_i,$$

where the x's are the covariates, $\beta$'s are the corresponding fixed effects, z's are covariates for the random effects, $\gamma_{Batch} \sim N(0, \sigma_{Batch})$ is the random effect for the Batch variable, and $\gamma_{Plate} \sim N(0, \sigma_{Plate})$ is the random effect for the Plate variable. Finally, $\epsilon_i \sim N(0, \sigma_\epsilon)$ is the error term.

The models were fitted using the lmer function from the R package lme4. The elimination was made using the step function from the lmerTest R. The only term dropped was the interaction between Rate and Alcohol.

Student's t-tests were also performed to determine statistically significant differences (p=0.05) between samples tested in the positive/negative solution screening experiments and vial freezing experiment sections described above.

Example 3

Lymphocytes (Jurkat cells) were prepared as described in Example 2. Nine experimental solutions were tested in each generation of algorithm iteration, with concentrations ranging between 0 and the maximums listed for each component in the solutions listed in Table 13 were tested against a solution of 10% DMSO. The cells were suspended in test wells of a 96-well plate. Plates were covered and placed in the control rate freezer. Cryopreservation was performed Thawing was performed in a 37° C. water bath. Plates were partially submerged for one minute before removing the silicone lid covering each well. After lid removal, plates were partially submerged again until samples were just thawed (appearance changed from opaque to clear), and viability dye was added to each plate immediately.

Calcein-AM aliquots were suspended in 4 mL of 20 μg/mL propidium iodide (PI) solution to a final concentration of 2 μM calcein-AM and 20 μg/mL PI. A volume of 50 μL of the calcein AM/PI viability dye was added to each well in the plate. Plates were covered and placed in the incubator for thirty minutes, and then fluorescence was measured using a plate reader (BioTek Instruments, Inc., Winooski, Vt.) with ex/em florescence spectra of 485/528 (calcein-AM/live) and 530/590 (PI, dead). Live and dead fluorescence measurements were recorded for each well.

The average live and dead cell counts after thawing were calculated for each solution for the test wells containing cells and control wells loaded with NORMOSOL-R (Hospira, Inc., Lake Forest, IL) or DMSO by comparing the in-well fluorescence to a control curve correlating fluorescence and known cell count. Viability prior to freezing and cells seeded per well were used to calculate the percentage of live cells recovered after thawing.

$$\text{Recovery (\%)} = \frac{\text{Live cells post thaw}}{\text{Live cells pre freeze}} \times 100$$

The average live cell recovery, standard deviation and p-value compared to the DMSO were calculated. The recovery was scaled to the average DMSO recovery rate for each plate and normalized to the average DMSO recovery value for each cooling rate. This correction allowed samples frozen on different plates at different cooling rates to be compared.

Results are shown in FIG. 16 and FIG. 17.

Example 4

Cell Culture

Human H9 ESC derived mesenchymal stem cells (MSCs) were isolated as previously described (Trivedi et al., 2008. *Exp Hematol* 36(3):350-359). MSCs were cultured in alpha-MEM (Gibco, Thermo Fisher Scientific, Waltham, Mass.) supplemented with non-essential amino acids (NEAA, Gibco, Thermo Fisher Scientific, Waltham, Mass.) and 10% FBS (qualified, Gibco, Thermo Fisher Scientific, Waltham, Mass.) in a 37° C. incubator at 5% $CO_2$. Cell confluency was maintained between 20% and 80% and media was changed every 3-4 days. Cells were used for experiments only between passages 8-12.

Cell Freezing

Cells diluted in blank solution (NORMOSOL-R, Hospira, Inc., Lake Forest, Ill.) were transferred to freezing vials and an equal volume of cryoprotectant solutions (Table 14)) at 2× their final concentrations were added to the vials stepwise. 10% DMSO controls were also prepared, in which cells suspended in MSC media were added to vials and DMSO introduced in the same stepwise fashion. For incubation studies, these cell suspensions were incubated at room temperature for 0 minutes, 30 minutes, one hour, two hours, or four hours before freezing according to the following protocol using a controlled rate freezer (Kryo 10 Series III, Planer PLC, Middlesex, United Kingdom):

1. Starting temp 20° C.
2. −10° C. per minute to 0° C.
3. Hold at 0° C. for 15 minutes
4. −1° C./min to −8° C.
5. −50° C./min to −45° C.
6. +15° C./min to −12° C.
7. −3° C./min to −100° C.

The final 1× concentrations present with cells for each solution tested are listed in the results section.

TABLE 14

| Solution name | Sucrose | Mannitol | Glycerol | Creatine |
| --- | --- | --- | --- | --- |
| SMC | 150 mM | 125 mM | | 12.5 mM |
| SGC | 150 mM | | 2.5% | 12.5 mM |
| SGC-A | 150 mM | | 684 mM | 25 mM |
| SGC-B | 300 mM | | 684 mM | 12.5 mM |

Thawing

Frozen vials were thawed in a 37° C. water bath. Vials were submerged halfway and agitated until only a miniscule ice pellet remained. Cells were assessed for viability immediately post thaw.

Viability and Functionality

Cells were assessed for viability at the conclusion of each experiment. Both pre-freeze and post-thaw vial counts were performed using acridine orange/propidium iodide (AO/PI). Briefly, cells were combined with AO/PI, loaded into a hemocytometer, and counted manually using a fluorescent microscope. A minimum of 200 total cells were counted for each sample. Viability was calculated for all samples by dividing the number of live cells by the number of total cells. Recovery was calculated directly by dividing the number of live cells post thaw by the number of live cells pre-freeze.

Osmolarity

Osmolarity of solutions was measured using an osmometer (OSMETTE, Precision Systems Inc., Natick, Mass.) for each solution and all measurements were repeated in triplicate.

Differential Scanning Calorimetry

Differential scanning calorimetry was performed on a differential scanning calorimeter (Q1000, TA Instruments, New Castle, Del.). Experimental solutions without cells were frozen to −150° C. using the following protocol:

1. Set starting temperature to 20° C.
2. Cool to −150° C. at 10° C./min
3. Hold for 3 min at −150° C.
4. Warm to 20° C. at 10° C./min Confocal Raman System Confocal Raman Microspectroscopy (CRM) measurements were conducted using a confocal Raman microscope system (Alpha 300 R, WITec Wissenschaftliche Instrumente und Technologie GmbH, Ulm, Germany) with a spectrometer (UHTS 300, WITec Wissenschaftliche Instrumente und Technologie GmbH, Ulm, Germany) and detector (DV401 CCD, Andor Technology Ltd., Belfast, United Kingdom) with 600/mm grating. The spectrometer was calibrated with a Mercury-argon lamp. A wavelength of 532 nm Nd:YAG laser powered at 10 mw was used as an excitation source. The laser was transmitted to the microscopy in a singer fiber. A 100× air objective (NA 0.90; Nikon Instruments, Melville, N.Y.) was used for focusing the 532-nm excitation laser to the sample. Samples were frozen using a controlled temperature stage as previously described (Dong et al., 2010. *Biophys J* 99(8):2453-2459).

Raman Measurement of Frozen MSC Cells

MSC cells were detached from the flask and washed with DPBS solution before being suspended in experimental solutions. Roughly 1 μL of cell suspension was placed on an aluminum sheet, covered with a piece of mica (Ted Pella, Inc., Redding, Calif.) and sealed with KAPTON tape (Dupont, Wilmington, Del.), to prevent evaporation/sublimation during each experiment. Cell suspensions were cooled to −6° C. at which point the sample was seeded by a nitrogen-cooled needle. Subsequently, the solution was cooled down at 3° C./min to −50° C. Ten Raman images of 30 μm×30 μm were collected.

Raman Image/Spectral Analysis

Spectrums at each pixel were analyzed using characteristic wavenumbers of common intracellular and extracellular materials (Table 15), and were integrated with background subtraction to result in an image. Spectra for the osmolytes used in the investigation overlapped with each other, so a broad peak centered at 850 $cm^{-1}$ was used to generate Raman images for all osmolytes. Data analysis was performed by Windows-based Project FOUR software plus version 4.0 (Microsoft Corp., Redmond, Wash.).

TABLE 15

Peak assignments for molecules of interest detected using Raman spectroscopy.

| Component | Frequency used for this study $cm^{-1}$ |
| --- | --- |
| Ice | 3120 (OH stretching) |
| Amide I | 1659 (C=O stretching) |
| Glycerol | 851 (C—C stretching) |
| Sorbitol | 878 (C—C=O stretching) |
| Glucose | 840 (C—C stretching) |
| Sucrose | 836 (C—C stretching) |
| Creatine | 840 (C—N torsion) |

Statistics

Averages plus or minus standard error of the mean are reported unless otherwise noted. Student's t-tests were performed to determine statistically significant differences ($p<0.05$) between samples tested in the osmolarity and sugar substitution studies.

Example 5

Cell Culture

The study involved the use of induced MSCs derived from H9 embryonic stem cells (H9-MSCs; Trivedi et al., 2008. *Exp Hematol* 36(3):350-359), which exhibit similar cell surface phenotype as bone marrow-derived MSCs (BM-MSCs), as well as appropriate in vivo migration and homing behavior in mouse models. Media used with H9 MSCs was composed of αMEM base (Thermo Fisher Scientific, Waltham, Mass.), 10% FBS (qualified), and 1% non-essential amino acids (Thermo Fisher Scientific, Waltham, Mass.). Culture flasks were coated with 0.01% porcine gelatin (Thermo Fisher Scientific, Waltham, Mass.) for a minimum of 2 hours before H9 MSC seeding. H9 MSCs were seeded in gelatin-coated flasks at a density of approximately 2,500 cells/cm$^2$. Cells were split when they reached 70% confluence and were used for experiments only between passages 8 to 12.

Optimization

The differential evolution algorithm used in this study was developed from strategy 2 (DE/local-to-best/1, balances robustness and convergence; Storn, R. & Price, K., 1997. *J Global Optimization* 11:341) and was coded in MATLAB. Details of the algorithm have been previously described (Pollock et al., 2016. *J Tissue Eng Regen Med*; doi:10.1002/term.2175). For this investigation, the algorithm was set to accept and provide output for discrete parameter vectors. The weight was set to 0.85, the crossover was set to 1, and cell attachment after freezing in each solution was used to iterate the cost function.

Surface Marker Characterization

Cells were suspended to a concentration of 1×10$^6$ cells/ml in media and stained with a panel of the following antibodies: mouse IgG1 anti-human CD73 (APC-conjugated, BD Biosciences, San Jose, Calif., clone AD2), mouse IgG1 anti-human CD90 (FITC-conjugate, clone 5E10, Molecular Probes, Eugene, Oreg.), mouse IgG1 anti-human CD105 (PE-conjugated, R&D Systems, Inc., Minneapolis, Minn. clone 166707) and mouse IgG1 anti-human CD45 (BV421-conjugated, clone HI30, BD Biosciences, San Jose, Calif.). Cells were incubated with antibodies for 30 minutes at 4° C. Flow cytometry was performed on a flow cytometer (LSR II, BD Biosciences, San Jose, Calif.) at low flow rate with the fine adjust knob five turns from max. At least 15,000 events were recorded for each sample. Cell populations were gated for forward and side scatter compared to unstained MSCs and CD45 expressing Jurkat cells as, respectively, negative and positive controls to establish boundaries for fluorescent signals.

Multilineage Differentiation

Differentiation of both fresh and post-thaw cells was induced using a chondrogenesis kit (STEMPRO, Thermo Fisher Scientific, Inc., Waltham, Mass.) and osteogenesis media and protocols. Chondrogenic micromass cultures were stained with 1% Alcian blue solution, while osteogenic cultures were stained with 2% Alizarin red solution.

Vial Freezing

Optimized solutions were prepared at double (2×) the final freezing concentration and added stepwise to cells in NORMOSOL-R (Hospira, Inc., Lake Forest, Ill.) at a 1:1 final volume ratio in a freezing vial (NALGENE, Nalge Nunc, Penfield, N.Y.). Control cells in media were similarly combined stepwise with DMSO at a 1:1 final volume ratio. Each of these vials was incubated at room temperature for 0 hours, one hour, or two hours. Experimental solutions were frozen using a 3° C./min cooling rate protocol described below, while DMSO solutions were frozen using a 1° C./min cooling rate protocol on a controlled rate freezer (Kryo 10 Series III, Planer PLC, Middlesex, United Kingdom). A multi-step procedure was followed in which the starting temperature was set at 20° C., and temperatures were subsequently modulated as follows: −10° C./minute to 0° C., hold at 0° C. for 15 minutes, −1° C./min to −8° C., −50° C./min to −45° C., +15° C./min to −12° C., and finally −1° C. or −3° C./min to −100° C.

Thawing

Samples were submerged in a 37° C. bath to just under cap level, and agitated until only a small ice crystal was present. The cells were combined with acridine orange/propidium iodide (AO/PI) and counted using a hemocytometer. Samples were diluted and the supernatant was aspirated after centrifugation. Cells were then prepared for cellular assays measuring proliferation, senescence or actin alignment, as well as biochemical studies using isolated DNA and RNA.

Attachment and Proliferation

Cell attachment of samples post-thaw was measured using a fluorescent plate reader. Samples were re-suspended in media and seeded in each of two gelatin-coated, 6-well plates. After two hours or 24 hours, these paired plates were washed with PBS, 1 µM calcein-acetoxymethyl (AM) dye was added, and then analyzed for fluorescence on a plate reader. Raw fluorescence values were used to calculate the number of live cells present in each well by correlating to a control curve of cells seeded at known densities. The live cell attachment was calculated by dividing the number of live cells present in the two-hour plated samples (calcein-AM plate reader fluorescence) by the number of live cells seeded pre-freeze.

Senescence

Cell senescence of samples post-thaw was measured using a luminescent plate reader. Samples were re-suspended in media and equal parts were added to each of four gelatin-coated 6-well plates. After incubation to permit attachment, plates were washed with PBS and two plates were analyzed at a time, one for proliferation and one for senescence. Beta-glo (Promega, Madison, Wis.) luminescent dye was added to measure senescence and 1 µM calcein-AM dye was added to measure proliferation. Plates were analyzed using a plate reader (BioTek Instruments, Inc., Winooski, Vt.) for luminescence (Beta-glo plate) and fluorescence (485ex/528em, calcein-AM plate), respectively. A relative measure of senescence is reported here by dividing the base-corrected luminescence (approximation of total senescence) per well by the base-corrected fluorescence (approximation of total cells per well). H9-MSCs treated for one hour on seven consecutive days with 100 µM t-BHP (to induce senescence) were used as a positive control.

DNA Isolation and Quantification

Pellets of cells were flash frozen in liquid nitrogen and then transferred for further DNA isolation and processing. Genomic DNA was isolated from the eight treatment group samples using QIAGEN DNeasy Blood & Tissue Kit according to the manufacturer's protocol. The purified DNA was quantified using NANODROP 2000 (Therm Fisher Scientific, Waltham, Mass.). The purity of the DNA was verified by determining the A260/A280 ratio for all samples and the ratio was consistently ~1.8.

DNA Hydroxymethylation by Dot Blotting

DNA samples were prepared by diluting total DNA to final amounts of 2 µg, 1 µg, 0.5 µg, and 0.25 µg with 0.1 M NaOH. The samples were denatured at 95° C. for 10 minutes and cooled quickly on an ice bath followed by neutralization with ammonium acetate. Loading sample volumes of 400 µl were prepared by adding equal volumes of 0.1 M NaOH and 2 M ammonium acetate to the denatured DNA. The nitrocellulose membrane was pre-wet in distilled water and placed on the microfiltration apparatus (BIO-DOT, Bio-Rad Laboratories, Inc., Hercules, Calif.) according to the manufacturer's recommendations. A vacuum was applied and the screws re-tightened to hold the apparatus together. The membrane was rehydrated with 0.1 M NaOH to prepare for sample application. With vacuum off, denatured DNA was added to sample wells, while all other wells were filled with the same volume of distilled water to obtain homogenous filtration. The samples were filtered by applying gentle vacuum, followed by an addition of 0.1 M NaOH to each well. The vacuum was applied again until wells were empty. The apparatus was disassembled and the membrane rinsed with 2×SSC. After air-drying, the membrane was blocked with 5% skimmed milk in PBS for one hour. The membranes were washed with PBS and incubated with anti-5hmC overnight. The next day, the membrane was washed with PBS and incubated with anti-rabbit secondary antibody. The blots were washed and developed using enhanced chemiluminescence (SUPERSIGNAL West Femto Maximum Sensitivity Substrate kit, Thermo Fisher Scientific, Waltham Mass.) by auto-exposure settings on the CHEMIDOC Touch Imaging System (Bio-Rad Laboratories, Inc., Hercules, Calif.). Data were quantified by densitometry and analyzed using Image Lab software by applying background subtraction and approximated for linearity.

Gene Expression Analysis by Real-time Quantitative PCR and RNA Sequencing

Pellets of thawed samples described above were resuspended in QIAZOL lysis agent (Qiagen, Hilden, Germany) for further RNA isolation and processing. RNA was isolated using the miRNeasy Mini Kit as per the manufacturer's protocol for cultured cells and cell pellets. The purified RNA was quantified using a NANODROP 2000 (Therm Fisher Scientific, Waltham, Mass.) device to determine concentration.

For qRT-PCR studies, 800 ng of RNA was used for reverse transcription to make cDNA using SuperScript III First-Strand Synthesis System (Thermo Fisher Scientific, Waltham, Mass.). cDNA was diluted to a concentration of 4 ng/µl and real-time qPCR was performed with 10 ng cDNA per 10 µl reaction with QuantiTect SYBR Green PCR Kit (Qiagen, Hilden, Germany) on CFX384 Real-Time PCR detection system (Bio-Rad Laboratories, Inc., Hercules, Calif.). The list of genes and their primer sequences are provided in Table 1. Melt curves were analyzed using the comparative CT method (Schmittgen et al., 2008. *Nat Protoc* 3:1101-1108) with GAPDH as an internal control gene.

High-throughput mRNA sequencing was performed on RNA isolated from the eight sample groups followed by bioinformatics analysis as described previously (Dudakovic et al., 2014. *J Cell Biochem* 115:1816-1828; Dudakovic et al., 2015. *J Biol Chem* 290: 27604-27617). Gene expression is expressed in reads per kilobase pair per million mapped reads (RPKM). Sequencing data are available at National Center for Biotechnology Information using Gene Expression Omnibus accession number GSE88946.

Example 6

Sample Preparation

For Raman measurements, experiment solution was made by dissolving osmolyte into Dulbecco's Phosphate Buffered Saline (DPBS) solution. Single osmolyte solutions were prepared to a final concentration of 600 mM. Two multicomponent osmolyte solutions, SSE-A (450 mM sucrose, 60 mM sorbitol, 70 mM ectoine) and SSE-B (450 mM sucrose, 300 sorbitol, 105 mM ectoine), also were also prepared.

Lysozyme powder was dissolved into each solution reaching final concentration of 100 mg/ml and then refrigerated. Lysozyme in DPBS solution was used as control. For DSC measurements, experiment solution was made by dissolving osmolyte into 20 mM HEPES buffer and the concentration of osmolyte in each solution remained same as in DPBS solution. Lysozyme powder was dissolved into each solution reaching final concentration of 1 mg/ml and kept refrigerated. Lysozyme in HEPES buffer was used as control. The pH of solutions was 7.3 measured by Beckman 350 meter.

TABLE 16

Denaturation temperature $T_m$ of lysozyme heating in various osmolyte solution

| Osmolyte | Denaturation temperature $T_m$ ° C. |
|---|---|
| SSE-A | 75.0 |
| SSE-B | 78.9 |
| Ectoine | 79.6 |
| Sorbitol | 83.1 |
| Sucrose | 84.4 |
| HEPES | 85.1 |

Confocal Raman System

Confocal Raman Microspectroscopy (CRM) measurements were conducted using a confocal Raman microscope system (Alpha 300 R, WITec Wissenschaftliche Instrumente und Technologie GmbH, Ulm, Germany) with a spectrometer (UHTS 300, WITec Wissenschaftliche Instrumente und Technologie GmbH, Ulm, Germany) and detector (DV401 CCD, Andor Technology Ltd., Belfast, United Kingdom) with 600/mm grating. The spectrometer was calibrated with a Mercury-argon lamp. A wavelength of 532 nm Nd:YAG laser powered at 10 mw was used as an excitation source. The laser was transmitted to the microscopy in a singer fiber. A 100× air objective (NA 0.90; Nikon Instruments, Melville, N.Y.) was used for focusing the 532-nm excitation laser to the sample. Samples were frozen using a controlled temperature stage as previously described (Dong et al., 2010. *Biophys J* 99(8):2453-2459).

Differential Scanning Calorimetry

Differential scanning calorimetry was performed on a differential scanning calorimeter (Q1000, TA Instruments, New Castle, Del.).

Osmolyte solutions containing lysozyme were heated in order to determine the denaturation temperature of lysozyme. Experimental solutions were heated from room temperature to 90° C. at 1° C/min. Specific heat, $C_p$, was calculated from the heat flow data assuming $$C_p = \frac{1}{m}\frac{\delta Q}{\Delta T}.$$

$C_p$ as a function of temperature were analyzed using OriginPro software (OriginLab Corp., Northampton, MA) to subtract curve baseline. The midpoint temperature, Tm, was obtained as the temperature corresponding to the maximum specific heat value from the baseline and the denaturation temperature was assumed to be Tm[32].

Osmolyte solutions without lysozyme were also frozen in order to characterize phase changes observed in the solutions during freezing. Experimental solutions were frozen to −150° C. using the following protocol:
1. Set starting temperature to 20° C.
2. Cool to −150° C. at 10° C./min
3. Hold for 3 min at −150° C.
4. Warm to 20° C. at 10° C./min The heat release as a function of temperature was used to determine any phase transition such as glass formation or eutectic formation.

Statistics

Averages plus or minus standard error of the mean are reported unless otherwise noted. Student's t-tests were performed to determine statistically significant differences of ice crystal area and ellipticity between different osmolyte solutions ($P<0.01$), as well as α-helix peak intensity of lysozyme frozen in different osmolyte solution ($P<0.05$) and MSCs recovery in SSE-A and SSE-B solution ($P<0.05$).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure (s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A cryopreservative composition comprising:
a sugar component; and
a sugar alcohol component;
wherein total concentration of sugar alcohol components in the composition is between 0.1 M and 2 M;
with the proviso that the composition includes less than a cryopreservative amount of dimethyl sulfoxide (DMSO).

2. The cryopreservative composition of claim 1 wherein the sugar component is provided at a concentration of 0.1 mM to 300 mM.

3. The cryopreservative composition of claim 2 wherein the sugar component is provided at a concentration of 10 mM to 300 mM.

4. The cryopreservative composition of claim 1 wherein the sugar component comprises trehalose, fructose, sucrose or glucose.

5. The cryopreservative composition of claim 1 wherein the sugar alcohol component is provided at a concentration of 0.1 M to 1.4 M.

6. The cryopreservative composition of claim 5 wherein the sugar alcohol component is provided at a concentration of 0.1 M to 0.6 M.

7. The cryopreservative composition of claim 6 wherein the sugar alcohol component comprises sorbitol, ethylene glycol, inositol, xylitol, or mannitol.

8. The cryopreservative composition of claim 5 wherein the sugar alcohol component comprises glycerol at a concentration of 0.6 M to 1.4 M.

9. The cryopreservative composition of claim 1 further comprising an additive component comprising a small molecule.

10. The cryopreservative composition of claim 9 wherein the additive component is provided at a concentration of from 0.1 mM to 300 mM.

11. The cryopreservative composition of claim 10 wherein the additive component comprises an amino acid.

12. The cryopreservative composition of claim 10 wherein the amino acid comprises proline, valine, alanine, isoleucine, histidine, taurine, ectoine, betaine, dimethylglycine, ethylmethylglycine, or an RGD peptide.

13. The cryopreservative composition of claim 1 wherein less than a cryopreservative amount of dimethyl sulfoxide (DMSO) is an amount of DMSO that provides no more cryoprotection than the remaining components of the composition without the DMSO.

14. The cryopreservative composition of claim 1 further comprising a cell.

15. The cryopreservative composition of claim 14 wherein the cell is a cryopreserved cell.

16. The cryopreservative composition of claim 15 wherein the cell is a viable recovered cryopreserved cell.

17. A method of cryopreserving a cell, the method comprising:
adding a cell to the composition of claim 1;
freezing the composition;
storing the frozen composition at a temperature below 0° C.;
thawing the composition;
removing the cell from the thawed composition; and
culturing the cell under conditions effective for the cell to remain viable.

18. The method of claim 17 wherein freezing the composition comprises at least one round of cooling, re-warming, and further cooling.

19. A cryopreservative composition comprising:
a sugar component comprising a disaccharide; and
a sugar alcohol component;
wherein total concentration of sugar alcohol components in the composition is no more than 2 M;
with the proviso that the composition includes less than a cryopreservative amount of dimethyl sulfoxide (DMSO).

20. A cryopreservative composition comprising:
a sugar component comprising a disaccharide, the sugar component being provided at a concentration of up to 300 mM;
a sugar alcohol component at a concentration of 0.1 M to 2 M; and
less than a cryopreservative amount of dimethyl sulfoxide (DMSO).

* * * * *

UNITED STATES PATENT AND TRADEMARK OFFICE
CERTIFICATE OF CORRECTION

PATENT NO. : 10,314,302 B2  
APPLICATION NO. : 15/381530  
DATED : June 11, 2019  
INVENTOR(S) : Allison Hubel et al.

Page 1 of 1

It is certified that error appears in the above-identified patent and that said Letters Patent is hereby corrected as shown below:

In the Specification

Column 27, Lines 37-42 formula should read:

$$\begin{aligned} y_i = {} & x_{i,\text{Sugar}}\beta_{\text{Sugar}} + x_{i,\text{Rate}}\beta_{\text{Rate}} + \\ & x_{i,\text{Alcohol}}\beta_{\text{Alcohol}} + x_{i,\text{Additive}}\beta_{\text{Additive}} + \\ & x_{i,\text{Sugar}\times\text{Rate}}\beta_{\text{Sugar}\times\text{Rate}} + \\ & x_{i,\text{Sugar}\times\text{Additive}}\beta_{\text{Sugar}\times\text{Additive}} + \\ & x_{i,\text{Sugar}\times\text{Alcohol}}\beta_{\text{Sugar}\times\text{Alcohol}} + \\ & x_{i,\text{Rate}\times\text{Additive}}\beta_{\text{Rate}\times\text{Additive}} + \\ & x_{i,\text{Rate}\times\text{Alcohol}}\beta_{\text{Rate}\times\text{Alcohol}} + \\ & x_{i,\text{Additive}\times\text{Alcohol}}\beta_{\text{Additive}\times\text{Alcohol}} + \\ & z_{i,\text{Batch}}\gamma_{\text{batch}} + z_{i,\text{Plate}}\gamma_{\text{Plate}} + \varepsilon_i \end{aligned}$$

Signed and Sealed this  
Eighteenth Day of February, 2020

Andrei Iancu  
*Director of the United States Patent and Trademark Office*